(12) United States Patent
Kusano et al.

(10) Patent No.: US 8,841,261 B2
(45) Date of Patent: Sep. 23, 2014

(54) FUNCTIONAL POWDERY PRODUCT

(75) Inventors: Hajime Kusano, Okayama (JP); Masato Takatori, Okayama (JP); Norio Oga, Okayama (JP)

(73) Assignee: Hayashibara Co., Ltd., Okayama-Shi, Okayama (JP)

( * ) Notice: Subject to any disclaimer, the term of this patent is extended or adjusted under 35 U.S.C. 154(b) by 485 days.

(21) Appl. No.: 10/593,264

(22) PCT Filed: Mar. 14, 2005

(86) PCT No.: PCT/JP2005/004476
§ 371 (c)(1),
(2), (4) Date: Sep. 18, 2006

(87) PCT Pub. No.: WO2005/087182
PCT Pub. Date: Sep. 22, 2005

(65) Prior Publication Data
US 2007/0140984 A1 Jun. 21, 2007

(30) Foreign Application Priority Data

Mar. 17, 2004 (JP) .................................. 2004-076061

(51) Int. Cl.
*A61K 31/7028* (2006.01)
(52) U.S. Cl.
USPC ........................................................ 514/25
(58) Field of Classification Search
USPC ........................................................ 514/25
See application file for complete search history.

(56) References Cited

U.S. PATENT DOCUMENTS

| | | | |
|---|---|---|---|
| 3,463,763 A | 8/1969 | Griffiths | |
| 4,439,458 A | 3/1984 | Puri | |
| 5,024,831 A * | 6/1991 | Kurisaki et al. | 424/69 |
| 5,145,781 A | 9/1992 | Suzuki et al. | |
| 5,889,164 A | 3/1999 | Murase | |
| 2003/0170186 A1 * | 9/2003 | Geers et al. | 424/59 |
| 2003/0232091 A1 * | 12/2003 | Shefer et al. | 424/490 |
| 2007/0003502 A1 * | 1/2007 | Tanabe et al. | 424/70.13 |

FOREIGN PATENT DOCUMENTS

| | | | | |
|---|---|---|---|---|
| DE | 4339486 | * | 5/1995 | A61K 7/48 |
| EP | 0 461 827 A2 | | 12/1991 | |
| EP | 1103246 A1 | | 5/2001 | |
| FR | 2 349 327 A1 | | 11/1977 | |
| GB | 2 258 865 A | | 2/1993 | |
| JP | 56156299 A | | 12/1981 | |
| JP | 03-058790 A | | 6/1989 | |
| JP | 03-007593 A | | 1/1991 | |
| JP | 03-139288 A | | 6/1991 | |
| JP | 03-220267 A | | 9/1991 | |
| JP | 4013691 A | | 1/1992 | |
| JP | 4054110 A | | 2/1992 | |
| JP | 4182413 A | | 6/1992 | |
| JP | 04-073278 A | | 9/1992 | |
| JP | 6040845 A | | 2/1994 | |
| JP | 07-143876 A | | 6/1995 | |
| JP | 07-118287 A | | 9/1995 | |
| JP | 08-127587 A | | 5/1996 | |
| JP | 2002338942 A | | 11/2002 | |
| JP | 2003137734 A | | 5/2003 | |
| JP | 2004315429 A | | 11/2004 | |
| JP | 2005-095148 A | | 4/2005 | |
| WO | 0027362 | | 5/2000 | |
| WO | 02/10361 A1 | | 2/2002 | |
| WO | 02/24832 A1 | | 3/2002 | |
| WO | 02/072594 A1 | | 9/2002 | |
| WO | 03/011233 A1 | | 2/2003 | |
| WO | WO 2004/071472 | * | 8/2004 | A61K 7/00 |

OTHER PUBLICATIONS

Allen et al (Ansel's Pharmaceutical Dosage Forms and Drug Delivery Systems, p. 264, 2004).*
Szycher (High Performance Biomaterials: A Complete Guide to Medical and Pharmaceutical Applications, pp. 625-626, 1991).*
Jurg Hempel et al., "Quality and Quantity of Prevailing Flavonoid Glycosides of Yellow and Green French Beans (*Phaseolus vulgaris* L.)", J. Agric. Food Chem., vol. 44, 2114-2116, (1986) XP-002632963.
Database WPI Week 198201, Thomson Scientific, London, GB; AN 1982-01054E & Abstract for JP 56 156299 A (Hayashibara Biochemical Lab), Dec. 2, 1981, Abstract.
Dashevsky et al., A. N., "Investigations on the Absorption of Quercetin on a Medicinal Carbonic Adsorbent. Controlled Release and Stability", Die Pharmazie, Govi Verlag GMBH, Eschborn, DE, vol. 50, No. 7, Jul. 1, 1995, pp. 465-467, XP000511713, ISSN: 0031-7144.
Supplementary European Search Report of EP 05 72 0744 dated May 3, 2011.
"Latest Cosmetic Science (Saidhin Keshohin Kagaku), revised and enlarged edition II", (1992), published by The Yakuji Nippo Ltd.
"New Cosmetology (Shin Keshohingaku)", (2002), published by Nanzando Co. Ltd.
"Cosmetic and Toiletry Formulation, 2nd edition", (2001), vol. 8, published by William Andrew Publisher.
Official Action for EP Application No. 05 720 744.1-1458 dated Jun. 19, 2013.

* cited by examiner

*Primary Examiner* — Paul Zarek
(74) *Attorney, Agent, or Firm* — Browdy and Neimark, PLLC

(57) ABSTRACT

The present invention has objects to provide a functional powdery product prepared by allowing carriers to support one or more members selected from vitamin glycosides, and to provide external dermatological agents having satisfactory usability, which contain the above functional powdery products and effectively exert the functions of vitamins. These objects are solved by providing a functional powdery product prepared by allowing carriers such as saccharides to support one or more members selected from vitamin glycosides, and by providing external dermatological agents incorporated with the functional powdery products.

14 Claims, 1 Drawing Sheet

FUNCTIONAL POWDERY PRODUCT

TECHNICAL FIELD

The present invention relates to functional powdery products prepared by allowing carriers such as saccharides to support one or more vitamins such as vitamin A, vitamin B, niacin, pantothenic acid, ascorbic acid (vitamin C), vitamin E, vitamin P, and derivatives thereof; and to external dermatological agents incorporated with the functional powdery products.

BACKGROUND ART

It has been known that vitamins such as vitamin A, vitamin B, niacin, pantothenic acid, ascorbic acid (vitamin C), vitamin E, and vitamin P have antioxidant action, capillary-recruiting action, blood-pressure-lowering action, capillary-reinforcing action, blood-pressure-lowering action, blood-cholesterol-level-improving action, anti-allergic action, action of maintaining the health of the skin and mucosa, action of maintaining acuity, action of improving metabolism, or skin-whitening action. Because of these functional properties, vitamins are focused on as food additives and have been gradually used in a variety of fields. In the field of cosmetics, there has been an increased preference to natural products with satisfactory safeness, stability, and functions; and there appears a tendency of exploring commercial products in such a manner of applying these substances or compositions containing the same to various products. While retaining the physicochemical properties inherent to the above substances before glycosylation, such as physiological activities and ultraviolet-ray-absorbing actions (throughout the specification, it may be called "functions" as a whole, hereinafter), glycosides of glycosylated vitamins (throughout the specification, they may be called "vitamin glycosides" as a whole, hereinafter), prepared by glycosylating the above-identified vitamins and derivatives thereof (throughout the specification, they may be called "vitamins" as a whole, hereinafter), have a distinctively high water-solubility or stability and have a satisfactory safeness, compared with the above substances before glycosylation. As the form of these vitamin glycosides in use, those which are prepared by positively utilizing their high water-solubility and stability have been mainly proposed, for example, in Japanese Patent Kokai Nos. 58790/91, 7593/91, 13691/92, 156299/81, and 182413/92.

In the case of incorporating vitamin glycosides into external dermatological agents in the form of a powder, solid, or solid powder, there is found no proposal of incorporating such vitamin glycosides intact in a powder form, and as disclosed, for example, in Japanese Patent Kokai No. 137734/2003, it is employed a process for producing lipsticks, comprising mixing and emulsifying an oily component and a water phase, containing a glycosyl-hesperidin as a vitamin P glycoside, into a preparation in the form of water in oil. Thus, in the case of incorporating vitamin glycosides into external dermatological agents, aqueous solutions of vitamin glycosides are generally used. As one of the reasons that the vitamin glycosides are not used in a powder form, there is a problem of production quality that such vitamin glycosides are not only hard to be homogeneously dispersed but hard to be prepared into homogeneous products, when mixed intact with other powders before incorporated into external dermatological agents. In the case of using fat-soluble vitamins, they might not be directly prepared into powders. To exert their inherent functions, these vitamins may cause problems of affecting the handling of the resulting cosmetics or deteriorating the makeup with the cosmetics due to water or perspiration because these vitamins may be required for use in a quite larger amount depending on the final products, compared with the case used in the form of a liquid. As an example of a solid external dermatological agent directly incorporated with a relatively small amount of a substance in a powder form, there has been proposed a product incorporated with a powder, as an ultraviolet-absorbing agent, obtained by binding a phenolic compound to a silk powder to enhance the ultraviolet-ray-absorbing effect inherent to the silk powder (cf. Japanese Patent Kokai No. 338,942/2002), however, there still remains a problem of allowing vitamin glycosides to efficiently support on carriers at an adequate concentration to exert their satisfactory functions.

Conventional cosmetics in the form of a powder, solid, or solid powder have the defect that they absorb sebum and cause skin roughness and chapping after applied to the skin. To overcome this problem, many trials have been made in such a manner of incorporating into cosmetic materials a larger amount of oils; polyols such as sugar alcohols including glycerin, xylitol, sorbitol, and polyethylene glycol; and humectants such as amino acids including pyrrolidone carboxylic acid; or emollients such as higher alcohols, higher fatty acids, ester oils, and lanolin. However, the use of any of these may cause a strong sticky feeling and distinctively deteriorate the usability and the makeup durability, resulting in no obtention of satisfactory cosmetics. To overcome these defects, for example, Japanese Patent Kokai No. 40,845/94 proposes a trehalose-containing cosmetic in a solid powder form. However, the above-identified patent literatures never disclose both the possibility of effectively incorporating vitamin glycosides on carriers such as saccharides at a higher concentration and any external dermatological agents incorporated with powders having the above supported glycosides; and they neither disclose nor suggest that the external dermatological agents exhibit the functions of vitamins such as satisfactory ultraviolet-ray absorbability action, anti-inflammatory action, anti-allergic action, skin-whitening action, etc., for a relatively long period of time, compared with mere mixtures of such vitamin glycosides and carriers.

The present invention has a first object to provide a functional powdery product prepared by allowing carriers such as saccharides to support one or more vitamins such as vitamin A, vitamin B, niacin, pantothenic acid, ascorbic acid (vitamin C), vitamin E, vitamin P, and derivatives thereof; and has a second object to provide an external dermatological agent which contains the functional powdery product and effectively exerts the functions inherent to the above vitamins.

DISCLOSURE OF INVENTION

The present inventors energetically studied a method for incorporating vitamins to homogeneity into external dermatological agents in the form of a powder, solid, or solid powder. As a result, they newly found that one or more vitamin glycosides can be effectively supported on carriers such as saccharides at a higher concentration; powders supporting vitamin glycosides (hereinafter, it may be called "functional powdery products", throughout the specification) can be easily and homogeneously incorporated into external dermatological agents; and the external dermatological agents incorporated with the functional powdery products exert the functions inherent to the vitamin glycosides for a longer period of time than those which are prepared by merely incorporating the above vitamin glycosides into carriers without supporting on the carriers. Thus, the present inventors accomplished this invention.

BRIEF EXPLANATION OF THE ACCOMPANYING DRAWINGS

EXPLANATION OF SYMBOLS

Figure 1:
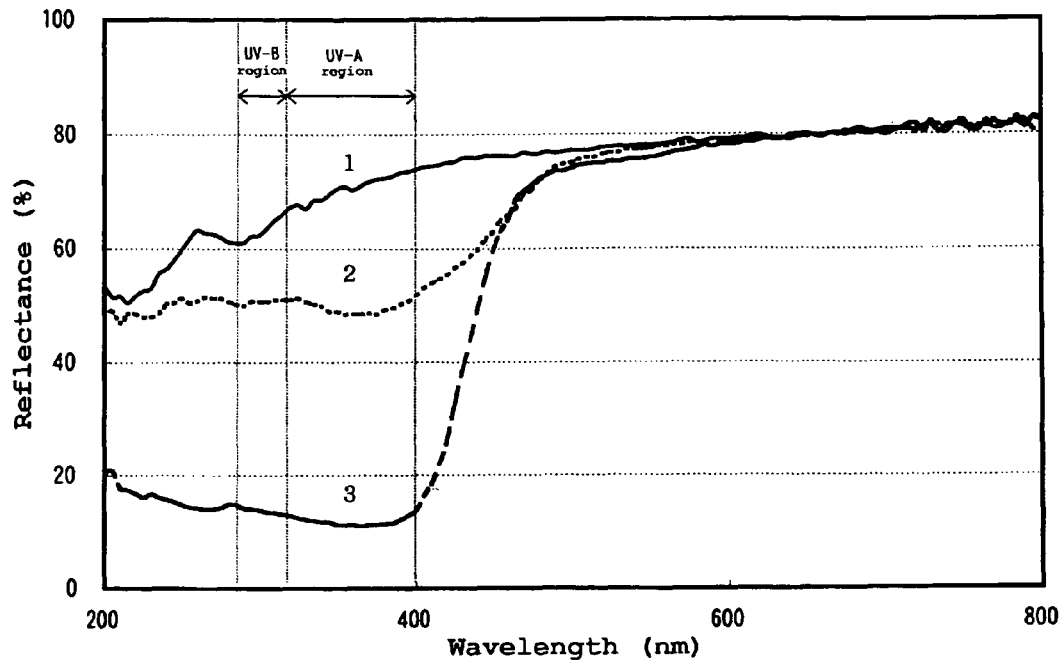
FIG. 1 is a figure which shows a spectral reflectance of a powdery product, prepared by allowing cellulose powder to support glycosyl-rutin, according to the present invention.

1. A spectral reflectance of cellulose powder alone.
2. A spectral reflectance of a powdery product prepared by mixing cellulose powder with powdery glycosyl-rutin in an amount of 2.5% to the cellulose powder.
3. A spectral reflectance of a powdery product prepared by allowing the cellulose powder to support glycosyl-rutin in an amount of 2.5% to the cellulose powder.
4. A spectral reflectance of silk powder alone.
5. A spectral reflectance of a powdery product prepared by mixing silk powder with powdery glycosyl-rutin in an amount of 10% to the silk powder.
6. A spectral reflectance of a powdery product prepared by allowing the silk powder to support glycosyl-rutin in an amount of 10% to the silk powder.

BEST MODE FOR CARRYING OUT THE INVENTION

The term "vitamins" as referred to as in the present invention means any vitamins to be glycosylated and derivatives thereof, for example, vitamin A, vitamin B, niacin, pantothenic acid, ascorbic acid (vitamin C), vitamin E, vitamin P, and their salts and derivatives. The term "vitamin B" as referred to as in the present invention means vitamin B family such as vitamin B1, vitamin B2, vitamin B6, and salts thereof. The term "vitamin E" as referred to as in the present invention means d-δ-tocopherol, dl-α-tocopherol, etc.; and the term "derivatives thereof" means dl-α-tocopherol acetate, dl-α-tocopherol linoleate, dl-α-tocopherol nicotinate, and dl-α-tocopherol succinate, as well as chromanol compounds as disclosed in, for example, Japanese Patent Kokai No. 118,287/95. The term "vitamin P or derivatives thereof" as referred to as in the present invention means substances which have the structure of quercetin, hesperetin, naringenin, or esculetin; and also means any substances as long as they retain the functions of the above substances and they can be glycosylated, such as rutin, hesperidin, naringin, esculetin, esculin, etc.

The vitamin glycosides used in the present invention mean those which are composed of the above-identified vitamins bound with one or more glycosyl residues, and which can directly or after decomposed by enzymes, etc., exert the functions of vitamins, independently of the type, binding site, or binding fashion of glycosyl residue. Independently of their origins and preparation methods, any vitamin glycosides can be used; and those which are prepared by fermentation method, enzymatic method, organic synthetic method, etc., and those which are commercially available vitamin glycosides or compositions containing the same can be arbitrarily used. These vitamin glycosides or compositions containing the same can be prepared by subjecting solutions of vitamins or compositions containing the same and adequate saccharides as substrates used for the following enzymes having saccharide-transferring activity to the action of an enzyme such as cyclomaltodextrin glucanotransferase (E.C. 2.4.19, may be abbreviated as "CGTase", hereinafter), α-glucosidase, α-amylase, β-galactosidase, α-galactosidase, lysozyme, or lipase to form glycosides having transferred glycosyl residues such as α-D-glucopyranosyl, β-galactopyranosyl, or β-D-chitosaminyl residue. The resulting reaction solutions obtained by these methods can be arbitrarily used intact as solutions containing vitamin glycosides or used after partially or highly purified, crystallized, and optionally further dried and pulverized. Concrete examples of such are as follows: By employing enzymatic methods as disclosed in Japanese Patent Kokai Nos. 58,790/91, 7,593/91, 13,691/92, 156,299/81, and 139,288/91 applied for by the same applicant as the present invention, solutions which contain rutin, hesperidin, naringin, esculin, ascorbic acid, or a composition containing any of them and further contain partial starch hydrolyzates such as starch or dextrin are allowed to the action of an enzyme with saccharide-transferring activity such as CGTase to bond one or more glucose residues to the above substances in order to form saccharide-transferred products such as α-glycosyl-rutin, α-glycosyl-hesperidin, α-glycosyl-naringin, α-glycosyl-esculin, α-glycosyl-L-ascorbic acid, etc. These preparation methods can be advantageously used on an industrial scale because they can produce the desired substances with only a relatively simple production facility efficiently at a lower cost by using abundant, lower-cost starch and partial hydrolyzates thereof as materials.

The term "functional powdery products" as referred to as in the present invention means powders of saccharides as carriers on which one or more of the above-identified vitamin glycosides and derivatives thereof are supported, and means those which have the functions of anti-inflammatory action, anti-allergic action, capillary-reinforcing action, blood-flow-improving action, or skin-whitening action inherent to the above-identified vitamins. Among which, the functional powdery products, having glycosides of vitamin P or ascorbic acid supported on carries, are particularly desirable because such glycosides have a relatively high water-solubility and can be supported on carriers such as saccharides efficiently at a relatively high concentration and also exert their functions efficiently for a relatively long period of time, compared with those which are prepared by merely incorporating these vitamin glycosides into carriers without supporting on the carriers. Glycosides of rutin, hesperidin, naringin, esculin, and esculetin are preferable as the vitamin P glycosides, and glucosides thereof are most preferable because of their safeness and easiness of their preparation methods. As the glycosides of ascorbic acid, ascorbic acid 2-glycoside is preferable, while ascorbic acid 2-glucoside is most preferable.

The preparation method for the functional powdery products of the present invention should not particularly be restricted to specific ones and includes conventional ones as long as they can support vitamin glycosides on carries such as saccharides. For example, the functional powdery products can be prepared by keeping carries such as saccharides in a suspended condition in solvents such as water and alcohols; dissolving one or more vitamin glycosides in the solvents, stirring the mixtures at a desired temperature for a prescribed period of time to make adsorption reaction; separating and drying the resulting functional powdery products from the solvents by appropriate methods such as centrifugal separation, filtration, and sedimentation; and optionally washing the separated functional powdery products with solvents and then drying the resultants. Depending on use, the functional powdery products thus obtained can be arbitrarily used intact without further separation and drying steps in formulations for external dermatological agents or the process for producing external dermatological agents.

The functional powdery products of the present invention can be prepared by supporting vitamin glycosides on carriers in combination with one or more colorants such as cyanine, squalillium, pyrylium, styryl, merocyanine, rhodacyanine, oxonol, coumarin, quinacridone, anthraquinone, polyazo, benzimidazolone, azo, anthraquinone, anthocyanin, chalcone, and carotenoid colorants, as well as other natural- or synthetic-colorants. Similarly as in glycosides of quercetin and/or hesperetin as colored vitamin glycosides, they can be advantageously used to modify the color tint of the above colorants when used in combination therewith. The modification of the color tint of the above colorants can be effectively exerted when the above colorants or those in a powder form, where the colorants are supported on carries, are mixed with the colored vitamin glycosides.

Examples of the natural colorants used in the present invention include safflower dye, gardenia yellow, glory bush dye, cochineal dye, turmeric dye, monascuscolor, beet dye, lac dye, madder color, perilla color, red cabbage color, red radish color, purple sweet potato color, elderberry color, blueberry color, red pepper color, annatto, spirulina color, cacao color, tamarind color, Japanese persimmon color, Koaliang color, caramel color, etc. The carriers used to prepare the powders, where the above-identified colorants are supported on the carriers, should not specifically be restricted; any of those which are used in the later-described preparation of the functional powdery products of the present invention can be arbitrarily used.

The amount of vitamin glycosides to be supported on carriers can be quantified by conventional determination methods depending on the vitamin glycosides, respectively. In the case that the amount is insufficient when judged from the data on determination, it can be controlled by repeatedly subjecting the vitamin glycosides to adsorption treatment for supporting on the carriers. Measurement of chromatic valence ($E^{1\%}$) enables to determine the amount of quercetin glycosides, hesperetin glycosides, and/or naringenin glycosides. The amount of ascorbic acid glycosides to be supported on carriers can be quantified by extracting the ascorbic acid glycosides from the carriers and subjecting the extract to high-performance liquid chromatography (HPLC) for quantitation. Accordingly, the carriers preferably used in the present invention are those which are insoluble or substantially insoluble in solvents. In the case that the adsorption ability of vitamin glycosides on carriers is low, they can be arbitrarily supported on the carriers in conventional manner by mordanting method using appropriate metal compounds. The term "chromatic valence ($E^{1\%}$)" as referred to as in the present invention means the absorbance at the maximum absorption wavelength for each substance in a suspension with a concentration of one percent by weight (throughout the specification, "% by weight" may be abbreviated as "%" hereinafter, unless specified otherwise) of quercetin glycoside, hesperetin glycoside, or naringenin glycoside.

The carriers preferably used in preparing the functional powdery products of the present invention should not specifically be restricted as long as they can support vitamin glycosides. Examples of such are listed as follows: Powders of saccharides such as acetyl cellulose, cellulose, starch, modified starch, agarose, agar, alginic acid, chitosan, chitin, agarose, and agar; powders of proteins such as silk, fibroin, collagen, gelatin, and casein; powders of derivatives of these saccharides and proteins; inorganic powders of hydroxyapatite, silica, and kaolin; and powders of synthetic high molecular polymers such as nylon, polyethylene, benzoguanamine, tetrafluoroethylene, di-styrene-benzene-pinhole-polymer, and polyamide high molecule (throughout the specification, "the powders used as carriers for the functional powdery products" may be called "powders", hereinafter). Among which, the powders of saccharides and proteins are preferable because of their origin as natural materials; the powders of saccharides are more preferable because of their stability against acids, alkalis, and heat; and the powders of cellulose are most preferable because of their adsorption efficiency. The form of the above-identified carriers should not specifically be restricted and any forms of spheres, porous spheres, plates, and fibers can be used. The carriers in a sphere form are desirable for obtaining the desired functions and effects by using adsorption materials in a possible lowest amount.

The average particle size of the functional powdery products of the present invention should not specifically be restricted as long as it is within the range of those for powdery products usually used in external dermatological agents. Considering the usability of external dermatological agents incorporated with the functional powdery products, those with an average particle size of about 0.01 to about 30 μm, preferably, about 0.1 to about 20 μm, and more preferably, about 2 to about 10 μm, are particularly desirable.

The term "supported/supporting" as referred to as in the present invention means that vitamin glycosides are bound to the surface of carriers such as saccharides (in the case that the saccharides are porous, the internal parts thereof are included in the surface) via a relatively weak power such as mainly hydrophilic or ionic bonding, an adhesion or chemical bonding, or a combination thereof.

From the functions and effects and the usability of the external dermatological agents, the total amount of vitamin glycosides supported on carriers is preferably within the range of 0.01 to 30% to the total amount of the functional powdery products, preferably, 0.1 to 20%, and particularly, 1 to 15%. In the case of the amount of less than 0.01%, the desired result could not be attained; while in the case of the amount of over 30%, the work efficiency in a supporting step may be lowered or it may problematically deteriorate the usability due to the formulation of external dermatological agents incorporated with the functional powdery products.

The functional powdery products thus obtained, where vitamin glycosides are homogeneously supported on the surface of carriers, have an improved solvent resistance, particularly, water resistance, heat tolerance, light absorbency, etc., by a large margin; and these effects become particularly distinct when saccharides are used as carriers. It is estimable that both the carriers and the vitamin glycosides supported on the carriers would have a common similar part in their structures. Since the carriers such as saccharides have a satisfactory humectancy, the functional powdery products prepared with such saccharides can be advantageously used as humectants for external dermatological agents. The functional powdery products containing supported vitamin glycosides such as quercetin glycosides, hesperetin glycosides, naringenin glycosides, and/or ascorbic acid glycosides, which absorb light in the ultraviolet ray region, can be advantageously used as ultraviolet-ray-absorbing agents. While the functional powdery products supporting vitamin glycosides such as quercetin glycosides and hesperetin glycosides, which absorb both lights in the ultraviolet-ray- and the visible-regions, can be arbitrarily used to modify the color tint of external dermatological agents when used in combination with other colorants such as pigments and dyes.

The functional powdery products of the present invention can be incorporated into external dermatological agents intact or optionally in the form of an additive for external dermatological agents incorporated with one or more pharmaceutically acceptable ingredients as external dermatological agents. Examples of such pharmaceutically acceptable ingredients include any of the later described substances without specific restriction; reducing saccharides, non-reducing saccharides, sugar alcohols, water-soluble polysaccharides, synthetic high molecular polymers, and substances having anti-oxidation action or emulsifying action. Among which, α,α-trehalose and saccharide derivatives thereof such as α-glucosyl α,α-trehalose, α-maltosyl α,α-trehalose, and α-maltotriosyl α,α-trehalose (disclosed in Japanese Patent Kokai No. 143,876/95 and Japanese Patent No. 3,182,679 applied for by the same applicant as the present invention), as well as saccharides containing the above saccharide derivatives (they all may be called "saccharide derivatives of α,α-trehalose", hereinafter) are particularly desirable because of their strong inhibitory action on the deterioration of vitamin glycosides, solidification inhibitory action on powders, and strong moisture-absorption inhibitory action. The additives for external dermatological agents thus obtained have a feature that they more effectively inhibit the functional reduction and solidification of the functional powdery products of the present invention during storage or transportation.

The amount of the functional powdery products of the present invention or the additives for external dermatological agents containing the same should not specifically be restricted as long as it can sufficiently exert the functions of vitamin glycosides and derivatives thereof. Considering the level of exerted functions and the usability of the functional powdery products or the additives for external dermatological agents containing the same, it is usually set to an amount of 0.01 to 20%, preferably, 0.1 to 10%, more preferably, 0.5 to 10% in terms of the functional powdery products in total against the total amount of each external dermatological agent.

To prepare the external dermatological agents of the present invention, the functional powdery products of the present invention or the additives for external dermatological agents containing the same can be incorporated into the desired external dermatological agents at any step from the stage of handling the starting materials to the stage of obtaining the final products. Concrete examples of such are, for example, conventional techniques such as mixing, kneading, dissolving, melting, dispersing, suspending, emulsifying, reverse micelle technique, penetrating, crystallizing, spreading, applying, spraying, injecting, soaking, and solidifying, which are appropriately selected. These techniques can be arbitrarily used alone or in an appropriate combination of two or more of them.

The term "pharmaceutically acceptable ingredients as external dermatological agents" as referred to as in the present invention should not specifically be restricted as long as they do not affect the functions of the functional powdery products of the present invention, and it includes substances having circulation-promotion action, anti-inflammatory action, antibacterial action, moisture-retaining action, skin-whitening action, ultraviolet-ray-absorbing action, ultraviolet-ray-scattering action, emulsifying action, astriction, anti-wrinkle action, cell-activating action, or percutaneous-absorption-promoting action; and/or oils and fats. One or more of these ingredients can be incorporated into the external dermatological agents of the present invention or the additives for external dermatological agents, and a plurality of such ingredients having a similar function and effect are arbitrarily incorporated in combination. The amount of these ingredients to be incorporated should not specifically be restricted as long as it does not affect the functions of the functional powdery products of the present invention, while exerting the desired functions of these ingredients. Usually, these ingredients are incorporated in an approximate amount used in conventional external dermatological agents.

The term "powder other than the functional powdery product" as referred to as in the present invention include non-organic powder such as talc, kaolin, sericite, white mica, synthetic mica, red mica, black mica, lithia mica, vermiculite, magnesium carbonate, calcium carbonate, diatomite, magnesium silicate, calcium silicate, aluminum silicate, barium silicate, strontium silicate, metal salts of tungstate, α-iron oxide, iron oxide hydrate, silica and hydroxyapatite; α,α-trehalose α,β-trehalose; saccharide derivatives of α,α-trehalose such as α-maltosyl α,α-trehalose and α-maltotriosyl α,α-trehalose; monosaccharides; disaccharides; oligosaccharides; dextrins; sugar alcohols; polymer powders such as nylon powder, polyethylene powder, benzoguanamine powder, tetrafluoroethylene powder, distyrene-benzene-pinhole polymer powder and polyamide polymer powder; agar powder; agarose powder; alginate powder; starch powder; processed starch; microcrystalline cellulose powder; chitin powder; chitosan powder; organic powders containing proteins such as silk, casein and gelatin; powders such as shikon (*Lithospermum* root) black powder, gardenia yellow powder, safflower red powder, red beat powder and ouni (deep yellow) powder (shikon black dyed powder supporting shikon dye can be referred to Japanese Patent Publication Nos. 73,278/92 or 220,267/91) supporting dyes such as shikonin derivatives including shikonin dye, gardenia dye, safflower dye, red beet dye and cochineal dye to the above organic powders; inorganic white pigments such as titanium oxide and zinc oxide; inorganic red pigments such as iron oxide (colcothar) and iron titanate; inorganic yellow pigments such as yellow oxide of iron and yellow ocher; inorganic violet pigments such as mango violet and cobalt violet; inorganic green pigments such as chromium oxide, chromium hydride and cobalt titanate; inorganic blue pigments such as ultramarine blue and Prussian blue; pearl pigments such as titanium oxide-coated mica, titamiun oxide-coated bismuth oxychloride, bismuth oxychloride, titanium oxide-coated talc, fish scale guanine, colored titanium oxide-coated mica; and metal powder pigments such as aluminum powder and copper powder; and powdered hydrophobes thereof. These materials can be freely used for the external skin preparation as long as they do not inhibit the functions of the functional powdery product of the present invention. They are incorporated in the preparation in an amount in the range of usually 0.0003-95%, preferably 0.01-80%, more preferably 0.01-75% by weight.

Examples of substances having blood flow-promoting effect incorporated into the external dermatological agent of the present invention are sialid, ginseng, ginkgo, ginger, garlic, angelica, arnica, fennel, *plectranthi herba*, *Nasturtium officinale*, chamomile, Roman chamomile, carrot, gentian, burdock, rice, crataegi fructus, "shiitake", *Crataegus oxyacantha*, juniper, *Cnidium rhizome*, thyme, clove, citrus unshiu peel, Japanese angelica root, persicae semen, *Paulownia* bark, butche's broom, grape, peony, horse chestnut, balm mint, *Citrus junos*, loquat, coix seed, rosemary, rose hips, citrus unshiu peel, Japanese angelica, peach, apricot, walnut, horsetail, calamus root, aloe, *Plectranthi herba*, gentian, capsicum and *Citrus junos*; hesperidin; glycosyl-hesperidin; rutin; glycosyl-rutin; acetylcholine; carpronium chloride; diphenhydramine hydrochloride; γ-oryzanol; l-menthol; cepharanthine; vitamin E or vitamin E derivatives including d-δ-tocopherol, dl-α-tocopherol, dl-α-tocopherol acetate, dl-α-tocopherol linoleate, dl-α-tocopherol nicotinate, dl-α-tocopherol succinate and vitamin E nicotinate; minoxidil; nicotinic acid amide; vanillylamide nonylate; carpronium chloride, or carbon dioxide. The amount of the substances is not specifically restricted as long as the substances do not inhibit the functions of the functional powdery product of the present invention. It is usually 0.001-5%, preferably 0.01-2% to the total amount of the external dermatological agent. In the case of less than 0.001%, they are not expected to exert the desired effect. In the case of more than 5%, they are not dose-dependently effective. When used in a hair tonic containing these substances as effective ingredients, the amount of the substances is not specifically restricted as long as the substances do not inhibit the functions of the functional powdery product of the present invention. It is usually 0.001-5%, preferably 0.02-3%. The term "plant or plant ingredient" as referred to as in the present invention means crushed materials from plant bodies such as leaves, stems, roots, flowers, fruits and bark; and extracts such as essence, essential oils, oils, fats and tinctures, obtained by treating with a solvent from plant materials. The resulting materials are optionally purified roughly or completely. The term "substance having blood flow-promoting effect" as referred to as in the present invention includes substances having the effect on expanding the blood vessels to promote blood circulation. In addition, it also includes substances having the effect on inducing a factor having blood flow-promoting effect with a local administration. Examples of such substances are capsici tincture, zingiberis tincture, kantiris tincture and wanyl norylate.

Examples of substances having antiinflammatory effect are allantoin or derivatives thereof such as allantoin acetyl-dl-methionine, allantoin chlorhydroxy aluminum, allantoin dihydroxy aluminum and allantoin polygaracturonate; glycyrrhetin or derivatives thereof such as glycyrrhetinic acid, glycyrrhizinic acid, allantoin glycyrrhetinate, glycerin glycyrrhetinate, stearyl glycyrrhetinate, glycyrrhetinyl stearate, disodium 3-succinyloxyglycyrrhetinate, dipotassium glycyrrhizinate and monoammonium glycyrrhitinate; pantothenic acid or derivatives thereof such as pantothenyl alcohols, pantothenyl ethylethers, acetylpantothenyl ethylethers, benzoil pantothenyl ethylethers, calcium pantothenate, sodium pantothenate, acetyl pantothenyl ethylethers, pantothenyl ethylether benzoate, and pantethine; vitamin E or derivatives thereof such as d-α-tocopherol, dl-α-tocopherol, dl-α-tocopherol acetate, dl-α-tocopherol linoleate, dl-α-tocopherol nicotinate, and dl-α-tocopherol succinate; L-ascorbic acid or derivatives thereof such as L-ascorbic acid glycoside including L-ascorbic acid 2-glucoside, acyl derivatives of L-ascorbic acid glycoside, ascorbyl tetrahexyldeconate, ascorbic acid tocopherol phosphate diesters (binding L-ascorbic acid to tocopherol via phosphoryl group), L-ascorbic acid sulfate esters, ascorbyl dipalmitate, ascorbyl palmitate, stearyl L-ascorbate, L-ascorbyl phosphate, ethyl L-ascorbate, acyl derivatives thereof; alkali metal or alkaline earth metal salts thereof; pyridoxine hydrochloride; menthol; biotin; camphor; turpentine; zinc oxide; azulene; quaiazulene and derivatives thereof; mefenamic acid or derivatives thereof; phenylbutazone or derivatives thereof; indomethacin or derivatives thereof; ibuprofen or derivatives thereof; ketoprofen or derivatives thereof; α-aminocapronic acid; sodium diclofenac; diphenhydramine; tranexamic acid or derivatives thereof; dexamethasone; cortisone or esters thereof; hydrocortisone or esters thereof; adrenal cortical hormone such as prednisone and prednisolone; antihistamic agent; esculin; esculetin or derivatives thereof; rose fruit; *Bistorta Major*; turmeric; *Hypericum erectum*; phellodendron bark; glycyrrhiza; *Lonicera japonica*; watercress; comfrey; acanthopanacis bark; sage; *lithospermum* root; white birch; tian cha; tea leaf; *Calendula officinatis*; elderberry; *Typha angustifolia; Sapindus mukurossi*, eucalyptus extract, broccoli, Japanese angelica root, loquat, chamomile, wormwood, aloe, ginseng, indigo, phellodendron bark powder, *Myrica rubra* bark, gambir, sweet hydrangea leaf, *Althea officinalis* root, arnica, echinacea, *Plectranthi herba, scutellaria* root, barley, St. John's wort, orange, Japanese valerian, Roman chamomile, *Artemisia caplillaris*, cucumber, gardenia, *Sasa albo-marginate*, gentian, geranium herb, burdock, *Xanthoxylum piperitum*, labiate, linden, peony root, ivy, juniper, peppermint, *Cnidium rhizome*, sialid, sage, mori cortex, jujube, thyme, *Benincasae semen, Calendula officinalis*, persicae semen, houttuynia, cordata, *Potantilla tormentilla*, parsley, mint, nettle, sandalwood, Butcher's bloom, grape, safflower, peony, linden, horse chestnut, peach, cornflower, wormwood, lavender, rosemary, rose hips, carrot and Japanese angelica root. It also includes α,α-trehalose, cyclic tetrasaccharide and/or saccharide derivatives thereof (hereinafter, it is simply called "cyclic tetrasaccharide".), which is disclosed by the same applicant in International Patent Publication Nos. WO 02/24832, WO 02/10361 and WO 02/072594, and Japanese Patent Kokai No. 304964/2003, and saccharide derivatives of α,α-trehalose. The amount of the substances is not specifically restricted as long as the substances do not inhibit the functions of the functional powdery product of the present invention. The amount of the substance is not restricted as long as it exhibits antiinflammatory effect against dermatitis alone or in combination with other substances. It is usually 0.001-5%, preferably 0.01-3% to the total amount of the external dermatological agent. In the case of less than 0.001%, they are not expected to exert the desired effect. In the case of more than 5%, they are not dose-dependently effective. When the ingredients are known to be in plant tissues such as glycyrrhizin in glycyrriza, they can be used in the present invention as long as they are properly prepared as extracts of plants containing thereof.

"Substances having anti-bacterial effect" is not specifically restricted and can be selected from substances having antibacterial effect acceptable to external dermatological agents. Examples of such substances are lower alcohols such as ethanol; benzoic acid or its salts or esters; alkyldiaminoglycine hydrochloride; photosensitizing dye such as pionin (KANKO-SO No. 201); chlorcresol; chlorbutanol; salicylic acid or salts thereof; sorbinic acid or salts or esters thereof; dehydroacetate or salts thereof; trichlorohydroxy phenyl ether; paraoxybenzoic ester; sodium paraoxybenzoate; phenoxyethanol; phenol; sodium lauryl aminoethyl glycine; resorcin; zinc-ammonia-silver substitutional zeolite; pantothenyl ethyl ethyl benzoate; isopropyl methyl phenol; cetylpyridium chloride; benzalkonium chloride; benzethonium chloride; chlorhexidine hydrochloride; orthophenylphenol; sodium orthophenyl phenoxide; chlorhexidine gluconate, cresol, chloramine-T, chlorxylenol, chlorphenesin, chlorhexidine, 1,3-dimethylol-5,5-dimethlhydantoin, alkylisoquinolinium bromide, thianthol, thymol, trichloro carbanilide, parachlorphenol, halocarban, hinokithiol, zinc pyrithione, methyl chloro isothiazolinon/methylisothiazolin solution, N,N''-methylenebis[N'-(hydroxymethyl-2,5-dioxy-4-imidazolinyl)urea], 2-(p-dimethylaminostyryl)-3-heptyl-4-metyl-thiazolinium iodide, imidazolidinyl urea, dimethylol dimethyl hydantoin, glutaraldehyde, jamal II, bisabolol, chlorhexidine gluconate, isopropyl methyl phenol, phenoxy ethanol, or plants or their components having an antibacterial effect such as tea oil, propolis, *Sapindus mukurossi*, asparagus, aloe, gingko, turmeric, echinacea, *Plectranthi herba*,

*Scutellaria radix, Coptis rhizome, Hypericum erectum*, clusiaceous, orange, *Artemisia capillaris*, gardenia, *Sasa albomarginate, Sophora angustifolia*, grapefruit, *Geranium thunbergii, Xanthoxylum piperitum, lithospermum* root, labiate, white birch, *Lonicera japonica, Achillea millefolium*, peppermint, *Cnidium rhizome*, sage, mori cortex, thyme, clove, *Calendula officinalis*, peony, hop, mint, peach, eucalyptus, lavender, rose hips, rosemary, wormwood, peony root, calamus and *Saponaria officinalis*. The amount of the substances is not specifically restricted as long as the substances do not inhibit the functions of the functional powdery product of the present invention and exert the antibacterial effect alone or in combination with other substances. It is usually 0.0001-3% to the total amount of the external dermatological agent. In the case of less than 0.001%, they are not expected to exert the desired effect. In the case of more than 2%, they are not dose-dependently effective.

Examples of substances having moisturizing effect are mucopolysaccharides such as hyaluronic acid, chondroitin sulfate, delmatan sulfate, heparan sulfate and heparin, or derivatives or salts thereof; ceramide; peptides or proteins such as collagen, elastin, fibronectin, keratin, gelatin and casein, or derivatives or hydrozate thereof; amino acids such as glycine, alanine, valine, serine, threonine, methionine, phenylalanine, leucine, tyrosine, proline, isoleucine, tryptphan, hydroxyproline, theanine, ornithine, citrulline, asparagine, aspartic acid, glutamine, glutamic acid, arginine, histidine, lysine, hydroxylysine, cysteine, cystine, acylglutamate and γ-polyglutamic acid, or derivatives thereof; pyrrolidone carbonate; pearl essence; reducing or nonreducing saccharides such as powder starch hydrolyzates, xylose, glucose, fructose, maltose, sucrose, lactose, palatinose, isomerized sugar, honey, maple sugar, brown sugar, glycosyl-sucrose-containing syrup, maltooligosaccharide, dextrin, isomaltooligosaccharide, galactooligosaccharide, fructooligosaccharide, nigerooligosaccharide, galactosylglucoside, lactosucrose, α,α-trehalose, α,β-trehalose (neotrehalose), β,β-trehalose (isotrehalose), cyclic tetrasacchaeide, saccharide derivatives of α,α-trehalose and starch; sugar alcohols such as erythritol, pentaerythritol, sorbitol, xylitol, maltitol, isomaltitol, lactitol, panitol, maltotriitol, maltotetraitol and maltopentaitol; gums such as pullulan, levan, sodium arginate, agar, gum Arabic, guar gum, tragacanth gum, xanthane gum, carrageenan and locust bean gum; water-soluble polymers such as pectin, methyl cellulose, carboxy methyl cellulose, polyvinyl alcohol, polyvinyl pyrrolidone, polydextrose and polyacrylic acid; polyols such as sugar esters, dextrin derivatives, glycerin, 1,3-butylene glycol, 1,4-butylene glycol, dipropylene glycol, polyethylene glycol, propylene glycol and amylene glycol; seaweeds such as coralline; plants or extracts thereof having moisturizing effect such as aloe, hamamelis, *Xanthoxylum piperitum, Artemisia vulgaris*, kava-kava, Asian ginseng, aloe, nettle, fennel, witch hazel, turmeric, *Lotus corniculatus, Phellodendron amurense, Hypericumerectum*, rice, chamolile, *Artemisa capillaris*, kiwi, cucumber, *Sophora angustifolia*, grape, gardenia, comfrey, *Saponaria officinalis*, rehmannia root, labiate, peony root, white birch, horsetail, linden, sage, sialid, *Cnidium rhizome*, mulberry, soybean, thyme, Japanese angelica root, *Calendula officinalis*, parsley, coix seed, Butcher's bloom, loofah, hop, horse chestnut, balmmint, peach, saxifrage, bramble, lavender, *Astragalus sinicus*, rose, *Rose multiflora*, rosemary, glycyrrhiza, tea leaf (green tea, black tea, oolong tea), lily, barley, wheat, apricot, oat, *lithospermum* root, lemon, quince, orange, strawberry, safflower, gentian, mint, spearmint, peppermint, *Sapindus mukurossi*, eucalyptus, *Lamium album*, pine, cornflower, *Sanguisorba officinalis*, avocado, seaweed, grapefruit, prune, lime, *Citrus iunos, Coptis rhizome*, cypress, peony, olive, sunflower, jojoba, macadamia nut, *Limnanthes alba*, camellia, almond, cacao and sesame. The amount of the substances is not specifically restricted as long as the substances do not inhibit the functions of the functional powdery product and exert the moisturizing effect alone or in combination with other substances. It is usually 0.1 or more, preferably 0.5% to total amount of the external dermatological agent. Upper limit of the substances is not specifically restricted as long as the substances do not inhibit the functions of the functional powdery product and can be used in a desired amount depending on the purpose of the objective external dermatological agent. The upper limit is usually 40% or less, preferably 20% or less to total amount of the external dermatological agent.

Saccharide mixtures containing saccharide derivatives of α,α-trehalose such as α-glucosyl α,α-trehalose, α-maltosyl α,α-trehalose and α-maltotriosyl α,α-trehalose or containing saccharides hydrogenated from reducing saccharides coexisting during processing steps are preferably used as materials having a moisture retaining property for the external dermatological agent of the present invention because they can stabilize the functional powdery product of the present invention and improve skin feeling lowered possibly depending amount of functional powdery product or shape of the external dermatological agent as well as protect skins from external stress such as ultraviolet, suppress sticky feeling when the external dermatological agent is used, and have an effect on smoothening skins and hairs as a feel improving agent. Saccharide mixture containing about 50% or more of α-maltosyl α,α-trehalose, 5-25% of other saccharide derivatives of α,α-trehalose, 25-45% of sugar alcohols of maltooligosaccharides including sorbitol, maltitol, maltotriitol, mantotetraitol and maltopentaitol is more preferably used because it has the effect on enhancing the functions of the functional powdery product of the present invention as well as satisfactory effects on moisture retaining, suppression of sticky feeling for external dermatological agents, anti-inflammation, protection or activation of cells, and keeping quality. A crystalline form of α-maltosyl α,α-trehalose is advantageously used for external dermatological agents in the form of powder, solid or solid powder because it further has satisfactory effect on absorbing lipids and is an easily handling powder.

Examples of substances having whitening effect are L-ascorbic acid derivatives and/or alkali metal or alkaline earth metal salts thereof such as L-ascorbic acid, L-ascorbic acid glycosides including L-ascorbic acid 2-glucoside, acyl-derivatives of L-ascorbic acid 2-glycoside, ascorbyl tetrahexyldeconate, ascorbic acid tocopherol phosphate diester (binding L-ascorbic acid to tocopherol via phosphoryl group), L-ascorbic acid sulfate ester, ascorbyl dipalmitate, ascorbyl palmitate, stearyl L-ascorbate, L-ascorbyl phosphate, ethyl L-ascorbate, acylated derivatives thereof; lactic acid, kojic acid, ellagic acid or derivatives thereof and/or alkali metal salts or alkaline earth metal salts, tranexamic acid, phytic acid, glutathione, hydroquinone or derivatives thereof including arbutin, plants or ingredients thereof having whitening effect such as chamomilla ET, "RUCINOL®" (4-n-Butylresorcinol), chamomile extract, brown sugar extract, albutin (a kind of glycosyl hydroquinone), glycyrrhiza, mori cortex, uva-ursi, bilberry extract, houttuynia herb extract, deer horn shape *ganoderma lucidum* extract, iris, clove, turmeric, capsicum, karela, aloe, tea leaf, glycyrrhiza, *scutellaria* root, chamomile, mori cortex, pueraria root, *Xanthoxylum piperitum*, moutan bark, gingko, rose fruit, *Coptis rhizome, Hypericum erectum*, gardenia, *Sophorae radix*, rice, rice bran, asiasarum root, peonyroot, cnidium root, mori cortex, tea leaf, Japanese angelica root, *Calendula officinalis*, hamamelis, safflower, *Amethyst sage*, gambir, hackberry, *Diospyros kaki*, sage, Japanese radish, azalea, parsley, hop and coix seed; animal ingredients such as placenta extract; and inorganic substance such as sulfur. The amount of the substances is not specifically restricted as long as the substances do not inhibit the functions of the functional powdery product and exert the antioxidant effect alone or in combination with other substances. It is usually 0.001-5%, preferably 0.01-3% to the total amount of the external dermatological agent. In the case of less than 0.001%, they are not expected to exert the desired effect. In the case of more than 5%, they are not dose-dependently effective.

Examples of substances having antioxidant effect are plants or plants ingredients having antioxidant effect such as vitamin A or derivatives thereof, vitamin B or derivatives thereof, L-ascorbic acid or derivatives thereof, vitamin D or derivatives thereof, vitamin E or derivatives thereof, dibutyl hydroxy toluene, butyl hydroxy anisole, superoxide dismutase, mannitol, carotenoids, astaxanthin, rutin or derivatives thereof, rutin, hesperidin, quercetin, catechin, epicatechin, epigallocatechin, or derivatives thereof including saccharide derivatives, gallic acid or derivatives thereof, glutathione or derivatives thereof, glutathione, β-carotenes or derivatives thereof, ubiquinol, flavonoids, proanthocyanidin, polyphenols including grape seedpolyphenol, sweet hydrangea leaf, turmeric, rose fruit, echinacea, *Scutellaria* root, *Hypericum erectum*, Chinese gall nut, *Geranium thunbergii*, rice, rice bran, comfrey, *Xanthoxylum piperitum*, labiate, peonyroot, soybean, "natto" (soybeans fermented in their own bacteria), tea leaf, clove, loquat, peony, horse chestnut, saxifrage, rooibos, rosemary, spirulina, chlorella and dunaliella. In addition, they include bilirubin, cholesterol, tryptophan, histidine, thiotaurine and hypotaurine. The amount of the substances is not specifically restricted as long as the substances do not inhibit the functions of the functional powdery product and exert the antioxidant effect alone or in combination with other substances. It is usually 0.0001-5%, preferably 0.001-2% to total amount of the external dermatological agent. In the case of less than 0.0001%, they are not expected to exert the desired effect. In the case of more than 5%, they are not dose-dependently effective.

Examples of substances having UV-absorbing effect are benzoate compounds such as paraaminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethy PABA butyl ester; anthranilate compounds such as homomenthyl-N-acetylanthranilate; salicylate compounds such as amylsalicylate, menthylsalicylate, homomenthylsalicylate, octylsalicylate, phenylsalicylate, benzylsalicylate, p-isopropanol phenylsalicylate; cinnamate compounds such as octylcinnamate, ethyl-4-isopropylcinnamate, methy-2,5-diidopropylcinnamate, ethy-2,4-diisopropylcinnamate, methy-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethy-p-methoxycinnamate, cyclohexyl-p-methoxycinnamate, ethyl-α-cyano-β-phenylcinnamate, 2-ethylhexyl-α-cyano-β-phenylcinnamate and glyceryl mono-2-ethylhexanoyl-diparamethoxycinnnmate; benzophenone compound such as 2,4-dihydroxy benzophenone, 2,2'-dihydroxy-4-methoxy bebzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone and 4-hydroxy-3-carboxy benzophenone; 3-(4'-methylbenzylidene)-d,l-camphor, 3-benzylidene-d,l-camphor, urocanic acid, urocanic acid ethylester, 2-phenyl-5-methybenzoxazol, 2,2'-hydroxy-5-methylphenylbenzotriazole, 2-(2'-hydroxy-5'-t-octylphenyl) benzotriazole, 2-(2'-hydroxy-5'-methylphenyl)benzotriazole, dibenzalazine, dianisoylmethane, 4-methoxy-4'-t-butyldibenzoylmethane, rutin, hesperidin, quercetin, or derivatives thereof including saccharide derivatives. Examples of substances having UV-scattering effect are titanium oxide, zinc oxide, selenium oxide, zircomium oxide, iron oxide, or clay minerals such as kaolin, talc, mica and sericite. The amount of the substances is not specifically restricted as long as the substances do not inhibit the functions of the functional powdery product and exert the UV-absorbing effect alone or in combination with other substances. It is usually 0.0001-40%, preferably 0.01-20% to the total amount of the external dermatological agent. In the case of less than 0.0001%, they are not expected to exert the desired effect. In the case of more than 40%, they are not dose-dependently effective.

Substances having emulsifying effect are not specifically restricted. One or more such substances can be freely chosen from substances having detergent activity, which are illustrated with non-ionic surfactants and/or ionic surfactants. Examples of non-ionic surfactants are sorbitan fatty acid esters such as sorbitan monolaurate and sorbitan sesquiisostearate; glycerin fatty acid esters such as glycerin monooleate and glycerin monoisostearate; polyglycerin fatty acid esters such as diglycerylmonooeate and decaglyceryl diisostearate; polyoxyethylene sorbitan fatty acid esters such as polyoxyethylene sorbitan monooleate (6 E.O.) and polyoxyethylene sorbitan monooleate (20 E.O.); polyoxyethylene sorbit fatty acid esters such as polyoxyethylene sorbit monolaurate (6 E.O.) and polyoxyethylene sorbit tetraoleate (40 E.O.); polyoxyethylene glycerin fatty acid esters such as polyoxyethylene gryceryl monooleate (5 E.O.) and polyoxyethylene gryceryl monooleate (15 E.O.); polyethylene glycol fatty acid esters such as polyoxyethylene monoisostearate (10 E.O.) and polyoxyethylene monooleate (6 E.O.); polyethylene glycol difatty acid esters such as polyoxyethylene diisostearate (8 E.O.) and polyoxyethylene diisostearate (12 E.O.); polyoxyethylene alkyl ethers such as polyoxyethylene oleyl ether (7 E.O.) and polyoxyethylene oleyl ether (10 E.O.); polyoxyethylene polyoxypropylene alkyl ether such as polyoxyethylene(1)polyoxypropylene(4)alkylether; and polyoxyethylene caster oil/wax such as polyoxyethylene caster oil (20 E.O.) and polyoxyethylene caster wax (40 E.O.). In addition, they include propyleneglycol fatty acid esters or ethylene oxide derivatives, polyether denaturation silicone, trehalose derivatives such as trehalose mono-fatty acid esters, trehalose difatty acid esters, and saccharide derivatives of trehalose and fatty acid esters thereof, sucrose fatty acid esters, and saccharide derivatives such as alkylglucoside.

The ionic surfactants are classified into anionic, cationic and amphoionic surfactants. Examples of the anionic surfactants are higher fatty acids; alkyl sulfate esters such as alkyl benzene sulfate and α-olefin sulfate; polyoxyethylene alkyl ether sulfate; acyl N-methyl taurinate; alkyl ether phosphate ester; N-acyl amino acids; alkyl amide phosphate; alkyl ether carbonate; salts thereof including alkali metal salts, alkaline earth metal salts, alkanolamino ion salts, ammonium ion salts and basic amino acid salts. Examples of cationic surfactants are alkyl trimethyl ammonium chloride, dialkyl dimethyl ammonium chloride, benzalkonium chloride, and alkyl benzyl methyl ammonium. Examples of amphoionic surfactants are betaine type amphoionic surfactants such as betaine alkyl dimethyl aminoacetate, betaine alkyl amide propyl demethyl aminoacetate and 2-alkyl-N-carboxymethyl-N-hydroxyethyl imidazolium betaine; imidazoline type amphoionic surfactants; amino acid type amphoionic surfactants; and non-ionic surfactants such as polyoxyethylene type surfactants, polyalcohol ester type surfactants and ethylene oxide/propylene oxide block polymers. The substances having emulsifying effect also include high polymer type surfactants and substances having emulsifying effect such as polyvinyl alcohol, sodium alginate, starch derivatives, cyclodextrins, anhydrous crystalline maltose, tragacanth gum, lecithin, saponin, isoflavones, phosphatidyl serine, phosphatidyl ethanolamine and phosphatidyl choline.

The amount of the substances is not specifically restricted as long as the substances do not inhibit the functions of the functional powdery product alone or in combination with other substances. It is usually 0.0001-50%, preferably 0.01-40% to the total amount of the external dermatological agent.

Substances having astringent effect are not specifically restrictedas longas the substances have an astringenteffect. Example of the substances are menthol, camphor, alum, chlorohydroxy aluminum, ammonium chloride, allantoin aluminum salt, zinc sulfate, metal salts of ammonium sulfate such as aluminium potassium sulfate, zinc sulfophenate, naringin, naringin derivatives such as glycosyl-naringin, organic acid such as tannic acid, citric acid, lactic acid and succinic acid, in addition, plants or plants ingredients including gambir, *Sweet hydrangea* leaf, *Althea officinalis* root, aloe, fennel, rose fruit, St. John's wort, *Lamium album*, orange, sea weed, valerian, *Artemisa capillaris*, bramble, kiwi, gentian, *Geranium thunbergii*, Chinese gall nut, maybush, meadowsweet, white birch, crataegi fructus tree, bourtree, juniper, nosebleed, sage, thyme, tea leaf, *Potantilla tormentilla*, nettle, coltsfoot, grape, hop, horse chestnut, balm mint, cornflower, wormwood, apple, lemon, *Astragalus sinicus*, rosehip, *Lonicera japonica*, peony root, horse tail, clematis and ivy. The amount of the substances is not specifically restricted as long as the substances do not inhibit the functions of the functional powdery product and exert the astringent effect alone or in combination with other substances. It is usually 0.0003-10%, preferably 0.001-5% to the total amount of the external dermatological agent.

Substances having wrinkle-reducing effect are not specifically restricted as long as the substances have a wrinkle-reducing effect. Examples of the substances are retinoids (such as retinol, retinoic acid andretinal), pangamic acid, kinetin, ursolic acid, turmeric extract, sphingosine derivatives, silicon, silica, N-methyl-L-serine and mevalonolactone. The amount of the substances is not specifically restricted as long as the substances do not inhibit the functions of the functional powdery product and exert the wrinkle-reducing effect alone or in combination with other substances. It is usually 0.0003-10%, preferably 0.01-5% to the total amount of the external dermatological agent.

Substances having cell-activating effect are not specifically restricted as long as the substances have a cell-activating effect. Examples of the substances are amino acids such as γ-aminobutyric acid and ε-aminocaporonicacid, vitaminssuchasretinol, thiamine, riboflavin, pyridoxine chloride and pantothenic acids, α-hydroxy acids such as glycolic acids and lactic acid; tannin; flavonoids; saponin; allantoin; KANKO-SO No. 301; esculin, esculetin; esculetin derivatives; and plant components of "gagome" oarweed, rockweed, *Undaria pinnatifida*, "Ressoniku", *Nemacystus decipiens* or *Pterocladia capillacea*. The amount of the substances not specifically restricted as long as the substances do not inhibit the functions of the functional powdery product are exert the cell activating effect alone or in combination with other substances. It is usually 0.0003-10%, preferably 0.001-5% to the total amount of the external dermatological agent.

Substances having transdermal absorption-promoting effect are not specifically restricted as long as the substances have a transdermal absorption-promoting effect. Examples of the substances are urea, lactic acid, fruit acids, α-hydroxy acids such as glycolic acid, sulfur, β-hydroxy acids such as salicylic acid, oleic acid, undecanoinic acid, octanol, nonanol, menthol, thymol, limonene, dimethy sulfoxide (DMSO), dodecylmethyl sulfoxide, N,N-dimethyllacetamide, N,N-dimethyl formamide, sodium laurylsulfate, N,N-bis(2-hydroxyethy) oleylamine, polyoxyethylene (20) sorbitan monooleate, dodecyl dimethyl ammoniopropanesulfate, propyleneglycol, polyethyleneglycol, N,N-dimethyl-m-toluamide, DEET (diethyl-m-toluamide), laurocapram, 1-dodecylazacycloheptane-2-on, isopropyl myristate, isopropyl palmitate, N-(mono or di)-p-mentane-3-carboxyamide, 2-(2-methoxy-1-methylethyl)-5-methylcyclohexanol or azacycloalkane derivatives or cyclodextrin. The above substances can be used in combination with other substances. The amount of the substances is not specifically restricted as long as the substances do not inhibit the functions of the functional powdery product and exert the cell activating effect alone or in combination with other substances. It is usually 0.0003-20%, preferably 0.001-10%, more preferably 0.01-5% to the total amount of the external dermatological agent.

The external dermatological agent of the present invention optionally comprises other ingredients used for usual external dermatological agent. Examples of the ingredients are powders; oils; fats; edetic acid; di-, tri- or tetra-sodium edetate; sodium citrate; oxycarbonic acids such as lactic acid and sodium lactate, or alkaline metal salts thereof; chelating agents such as ethylenediamine tetraacetate or alkaline metal or alkaline earth metal salts thereof and sodium metaphosphate; antioxidants such as butylhydroxy toluene (BHT), butylhydroxy anisol (BHA) and propyl gallate; water; alcohols such as ethanol and isopropanol; oily substances such as liquid paraffin, VASELINE® (petroleum jelly), microcrystalline wax, squalane, ceramide, sweet almond oil, olive oil, hardened oil, caster oil, Japan wax, coconut oil, bees was, lanolin, carnauba wax and palm oil; sterols such as phytosterol, fatty acids such as lanolic acid, myristic acid, palmitic acid, stearic acid, isostearic acid and oleic acid, or triglyceride thereof; higher alcohols such as lauryl alcohol, cetanol, stearyl alcohol, oleyl alcohol and cholesterol; esters such as isopropyl myristate, myristyl myristate and isopropyl palmitate; other inorganic or organic acids such as phosphoric acid, α-hydroxy acids including citric acid, malic acid, tartaric acid, lactic acid and succinic acid, acetic acid, or salts thereof; inorganic or organic alkaline agent such as sodium hydrate, potassium hydrate and triethanolamine, or salts thereof (pH adjusting agent); fullerene or derivatives thereof; colorants such as yellow iron oxide, titan yellow and carthamin; vitamins such as thiamine, nicotinamide, riboflavin, L-ascorbic acid, pyrrolo-quinoline quinone, carotenoide, ergosterol and tocopherol; naringin; glycosyl-naringin; photosensitizing dyes such as KANKO-SO No. 101 (platonin), KANKO-SO No. 301 (takanal), KANKO-SO No. 401 and plarumin; tar colorants such as Red No. 104, Yellow No. 4, Yellow No. 5, Green No. 3, Blue No. 1, Blue No. 2, Red No. 202, Red No. 226, Red No. 227, Red No. 230, Orange No. 206, Orange No. 207, Yellow No. 202, Green No. 201, Green No. 204, Blue No. 201 and Green No. 205, synthetic lake colorants from carminic acid, laccaic acid, carthamin, brazilin and crocin; natural colorants; ingredients used in bath salts such as sulfur, sodium bicasbonate, sodium chloridem mint, mineral spring, sodium carbonate, sinter, borax, *Cnidium rhizome*, Japanese angelica root and *Schizonepetae herba*.

The oils and fats are not specifically restricted. Examples of the oils and fats are synthetic oils or fats such as medium chain triglyceride; plant oils or fats such as soybean oil, rice oil, rape oil, cotton oil, sesame oil, safflower oil, caster oil, olive oil, cacao oil, camellia oil, sunflower seed oil, palm oil, linseed oil, perilla oil, shea oil, sal oil, coconut oil, Japan wax, jojoba oil, grape seed oil and avocado oil; animal oils or fats such as mink oil, egg yolk oil, beef tallow, milk fat and lard; waxes such as bees wax, spermaceti, lanolin, carnauba wax and candelila wax; hydrocarbons such as liquid paraffin, squalene, squalane, microcrystalline wax, ceresin wax, paraffin wax and vaseline; natural and synthetic fatty acid such as lauric acid, myristic acid, stearic acid, oleic acid, isostearic acid and behenic acid; natural and synthetic higher alcohols such as cetanol, stearyl alcohol, hexyl decanol, octyl decanol and lauryl alcohol; esters or ethers such as isopropyl myristate, isopropyl palmitate, octyldodecyl myristate and choresterol oleate; and silicone oil.

The external dermatological agent can be used in combination with one or more members selected from the group consisting of lymphokines such as interferon-α, interferon-β, interferon-γ, tumor necrosis factor-α, tumor necrosis factor-β, macrophage migration inhibitory factor, colony stimulating factor, transfer factor and interleukin-2; hormones such as insulin, growth hormone, prolactin, erythropoietin, follicle stimulating hormone and steroids; antibiotics such as penicillin, erythromycin, chloramphenicol, tetracycline, streptomycin and kanamycin sulfate; immune regulating agents; immune activating agents; hemostatic agents; enzymes such as lipase, elastase, urokinase, protease, β-amylase, isoamylase, glucanase and lactase; plant extracts including fungus or herbs such as ginseng, aloe, mallow, iris, grape seed, coix seed, balmmint, nosebleed, loofah, lily, phellodendron bark, peonyroot, sialid, birch, loquat, chlorella, propolis extract, agariks, *Ganoderma lucidum*, deer horn shape *Ganoderma lucidum* and *Phellinus linteus*; animal extracts such as snapping turtle extract; seaweed extract such as *Enteromorpha compressa* extract and yellow green laver extract; flavangenol; royal jelly; galenicals; high intensity sweeteners such as dihydrochalcone, stevioside, α-glycosyl stevioside, rebaudioside, glycyrrhizin, L-aspartyl-L-phenylalanine methyl ester, acesulfame-K and sucralose, saccharin; minerals or compounds thereof such as calcium, magnesium, iron, manganese, cobalt, copper, zinc, phosphorus, selenium, fluorine and iodine; waters such as electron water, magnetized water, ionized water and clustered water.

If necessary, the external dermatological agent can also comprise one or more substances used for pharmaceuticals, quasi-drugs, cosmetics or toiletries, described in "Japanese Standard of Cosmetic Ingredients", "Supplement to the Japanese of Cosmetic Ingredients codex", "Japanese Cosmetic Ingredients Codex by Category", "Japanese Quasi-drug Ingredients Codex", "The Japanese Pharmacopoeia", "Supplement to the Japanese Pharmacopoeia codex", "Japanese Standards of Pharmaceutical Additive", "Japanese Standards of Herbal Medicine", "The Japanese Standards of Food Additives", "Latest Cosmetic Science (Saishin Keshohin Kagaku), revised and enlarged edition II", published by The Yakuji Nippo Ltd, in Jul. 10, 1992, "New Cosmetology (Shin Keshohingaku)", published by Nanzando Co. Ltd., in Jan. 18, 2002, or "Cosmetic and Toiletry Formulation, 2nd edition", Vol. 8, published by William Andrew Publisher, in 2001. Examples of such ingredients are pharmaceuticals, excipients, bases, emollients, cooling agents, astringents, refrigeratives, surfactants, emulsifiers, dispersing agents, solubilizing agents, solvents, alkaline chemicals, thichening agents, gums, film-forming agents, foaming agents, antifoaming agents, perfumeries, coloring agents, gloss-imparting agents, stabilizers, antiseptics, bactericides, discoloration inhibitory agents, antioxidants, hair treating agents, humectants, hair-protecting agents, tricyst activator agents, antielectrostatic agents, auxiary agents, solvents, solubilizing agents, plasticizers, suspending agents, buffering agents, sweeteners, refrigeratives, sweetening agents, binders, absorbents, propellants, coating agents, masticatories, fillers, softeners, adjusters, chelating agents, discoloration inhibitory agents, oils, fats, oil-soluble polymer, inorganic or organic pigments, inorganic or organic pigments treated with silicone or fluoro compounds, pigments such as organic dyes, photosensitizing dyes such as rumin, waxes, pore contracting agents, antiperspirants, deodorants, anti-wrinkle agents, anti-dandruff agents, sebum secretion inhibitors, antiseborrheic agents, horny layer removers, horny layer resolving agents, parakeratosis inhibitors, analgestics, torpents, antiplasmic agents, nutritional supplements, antiandrogenic agents, antihistamic agents, collagenase inhibitors, elastase inhibitors, hyaluronidase inhibitors, fibroblast activating agents, collagen-production promoting agents, tyrosinase inhibitors, anti-allergic agents, and hemastatic agents. If necessary, usual food ingredients can be used. The above ingredients can be used in any amount for the external dermatological agent of the present invention as long as they do not affect the desired effects of the present invention.

The term "external dermatological agent" as referred to as in the present invention includes cosmetics, quasi-drugs or pharmaceuticals, and further includes chemical products, industrial products, commodities and sundries having a possibility to directly contact with skins. Any form of the external dermatological agent can be used; which illustrated with solution form, resolvable form, emulsion form, powder-dispersion form, water-oil form, water-powder form or water-oil-powder form. The functional powdery product of the present invention can be freely used as base cosmetic, finishing cosmetic, skin cosmetic, cleansing cosmetic, face wash, toilet water, cream, milky lotion, pack, foundation, face powder, powder, rouge, eyebrow, eye and cheek care cosmetic, perfume, bath cosmetic, oral care cosmetic, tanning cosmetic, sun care cosmetic, makeup cosmetic, nail cosmetic, eye liner cosmetic, mouse and lip care cosmetic, oral care cosmetic, facial care cosmetic, cosmetic oil, fragrant cosmetic, body care cosmetic, hair care cosmetic, hair wash cosmetic, cosmetic soap, medicated soap, toothpaste, oral refrigerative, hircismus blocker, bath dusting powder, hair growth promoter, tonic, shaving cosmetic, sun screen, antiiching agent, wiping and cleaning agent, bactericide, disinfectant, decolorant and depilatory, further, preventing or treating agent for athlete's foot, hemorrhoids, acnes, wounds, burns, chilblains, rashes, festers, inflammations, infections, allergies, atopic diseases, ulcers or tumors in the form of a toilet water, lotion, milky lotion, cream, ointment, plaster, suspension, emulsion, paste, mousse, tic, solid, semisolid, powder, solid powder, mid-container forming powder, block, pencil, stick, jelly, gel, aerosol, spray, lozenge, pack or facemask. Examples of such cosmetics are cosmetic soaps, face cleansing creams, cleansing foams, cleansing creams, cleansing milks, cleansing lotions, cleansing oils, massage creams, cold creams, moisture creams, vanishing creams, hand creams, moisture lotions, cosmetic oils, liquid foundations, powder foundations, cake foundations, stick foundations, oily compact foundations, creamy foundations, cheek blushers, emulsified foundations, foundation cosmetics, body powders, creamy face powders, face powders, liquid face powders, solid face powders, paste face powder, talcum powder, loose shadows, baby powders, cheek colors, pencils, mascaras, lipsticks, lip creams, packs, shaving creams, after shaving creams, lotions, hand lotions, shaving lotions, after shaving lotions, sun screen creams, tanning oils, sun screen lotions, tanning lotions, softening toilet waters, astringent toilet waters, cleansing toilet waters, multi-layer toilet waters, facial shampoos, body shampoos, hair shampoos, hair-washing powders, hand soaps, facial rinses, body rinses, hair rinses, hair treatments, pilatories, tonics, tics, pomades, hair creams, hair liquids, hair tonics, set lotions, combing oils, combing oils for side hair, hair sprays, hair mousses, hair tonics, hair dyes, hair bleachers, color rinses, color sprays, permanent wave liquids, pressed powders, loose powders, eye creams, eye shadows, cream eye shadows, powder eye shadows, eye liners, eye brow pencils, mascaras, depilatory creams, perfumes, kneaded perfumes, powder perfumes, eau de cologne, deodorants, bath preparations, bath oils, bath salts, cosmetic oils, baby oils, nail colors, enamels, enamel removers, nail treatments, mouth washes, toothpastes, tooth powders, insect repellers, ointments for treating wounds, antibacterial creams, steroid ointments, and further, cataplasms in the form of sheet or film, laundry soaps or detergents for clothes, detergents for flower, detergents for kitchen and cleansers. Because the functional powdery product of the present invention is capable of easily and uniformly admixing cercetine glycoside, hesperidin glycoside, naringenin glycoside and/or ascorbic acid glycoside with the external dermatological agent in the form of powder, solid or solid powder, it is more advantageously used in such case.

Following experiments concretely explain Uv-absorbing ability of the functional powdery product of the present invention.

Experiment 1
Effect of Glycosyl-Rutin, Supported on Cellulose Powder, on UV-Absorption Property Following experiment was carried out to examine the effect of glycosyl-rutin, a vitamin P glycoside, supported on cellulose powder, on UV-absorption property. A functional powdery product, supporting glycosyl-rutin in an amount of 2.5% by weight to the total weight, prepared in the following Example 1, was injected into a cell for powdery sample to be fixed, and subjected to the diffused lighting system (condition: d(n–D) [O/d]) providing by Japanese Industrial Standards (Z 8722:2002, corresponding to the measurement of object color specified in items 1-3 in COLORIMETRY SECOND EDDITION Publication CIE No. 15.2, (1986) recommended by the International Commission on Illumination) using a spectrophotometer ("U-best 50" equipped with an integration sphere device (TIS-417 type), produced by JASCO Corporation) in order to measure spectral reflection of captured, diffusion-reflection light in an integral sphere. As a control, a sample consisting of cellulose powder and a sample prepared by uniformly mixing 2.5 parts by weight of glycosyl-rutin, which was the same as glycosyl-rutin supported on the cellulose powder, with 97.5 parts by weight of cellulose powder were similarly subjected to the above measurement for spectral reflection. The result is shown in FIG. 1.

As is evident from the result in FIG. 1, the cellulose powder supporting glycosyl-rutin had lower in a reflection of ultraviolet in the range of UV-B and UV-A than that of the cellulose powder or the mixture of cellulose power and glycosyl-rutin, revealing that it effectively absorbs ultraviolet ray (UV). Although the enhancing mechanism of such absorption is not clear, it can be thought that the cellulose powder, uniformly supporting glycosyl-rutin on its surface, more efficiently absorbs UV than the powder of glycosyl-rutin, having a big particle size, dispersed in the cellulose powder used as a carrier.

Experiment 2
Effect of Glycosyl-Rutin, Supported on Silk Powder, on UV-Absorption Property Following experiment was carried out in order to examine the effect of glycosyl-rutin supported on silk powder on UV-absorption property. A functional powdery product, supporting glycosyl-rutin in an amount of 10% by weight to the total weight, prepared in the following Example 2, was injected into a cell for powdery sample to be fixed, and measured their spectral reflection according to Experiment 1. The result is shown in FIG. 2.

Figure 2:
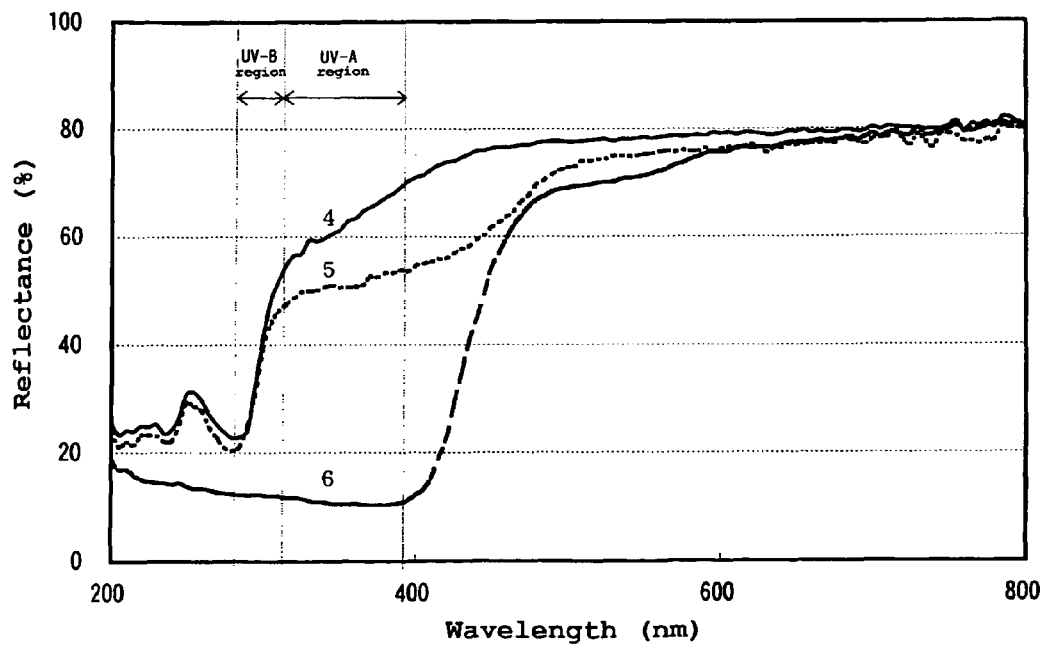
FIG. 2 is a figure which shows a spectral reflectance of a powdery product, prepared by allowing silk powder to support glycosyl-rutin, according to the present invention.

As is evident from the result in FIG. 2, the silk powder supporting glycosyl-rutin had lower a reflection of UV in the range of UV-B and UV-A than that of the silk powder or the mixture of silk power and glycosyl-rutin, revealing that it effectively absorbs ultraviolet ray. The results of Experiments 1 and 2 revealed that the cellulose powder more efficiently absorb ultraviolet than the silk powder when used as carriers in such a manner of being supported on a smaller amount of glycosyl-rutin.

The following Examples explain in detail the functional powdery products, additives containing the same for external dermatological agents, external dermatological agents incorporated with the additives containing the functional powdery products or the additives for external dermatological agent in detail. The present invention should not be restricted by the Examples.

Example 1

Functional Powdery Product

Twenty grams of crystalline cellulose ("AVICEL PH-M06", commercialized by Asahi Kasei Corporation) was admixed with 45 ml of purified water, stirred at an inner temperature of 10-15° C., admixed once with 5 ml of purified water containing 1 g of glycosyl-rutin ("αG-RUTIN", commercialized by Hayashibara Biochemical Laboratories, Inc.), and stirred at the same temperature for two hours. After the resulting solution was stirred at an ambient temperature for one hour, 19.5 g of the functional powdery product supporting glycosyl-rutin was collected by filtration and dried. 57.5 mg of the resulting dried functional powdery product was weighed and placed into a 50-ml volume of measuring flask, and then admixed and filled up with a solution containing ion exchanged water/ethanol (60/40 (v/v %)). The resulting solution was stirred by magnetic stirrer for 20 minutes to solve out the supported glycosyl-rutin. After removing insoluble powder by natural filtration, the resulting solution was subjected to measurement of absorbance at near 360 nm corresponding to absorption maximum of glycosyl-rutin using quartz glass cell with 1 cm of light path length to obtain 0.6509 of absorbance value and calculate 5.55 of chromatic valence ($E^{1\%}$). Chromatic valence of glycosyl-rutin used for coloring was 227. Therefore, the content rate of glycosyl-rutin in the obtained functional powdery product was calculated by 2.5% to total weight of the functional powdery product.

Example 2

Functional Powdery Product

Twenty grams of silk powder ("SILK POWDER", commercialized by Kanebo Ltd.) was admixed with 150 ml of purified water, stirred, admixed with 10 ml of purified water containing 6.4 g of glycosyl-rutin ("αG-RUTIN", commercialized by Hayashibara Biochemical Laboratories, Inc.) used in Example 1, and stirred for about one hour. 19.2 g of the functional powdery product supporting glycosyl-rutin was collected by filtration and dried. Since the product had chromatic valence of 23.3, the content rate of glycosyl-rutin in the obtained functional powdery product was calculated by 10% to total weight of the functional powdery product.

Example 3

Functional Powdery Product

Twenty grams of crystalline cellulose ("AVICEL PH-M06", commercialized by Asahi Kasei Corporation) was admixed with 45 ml of purified water, stirred at an inner temperature of 90° C., admixed with 5 ml of purified water containing 1 g of glycosyl-hesperidin ("αG-HESPERIDIN", commercialized by Hayashibara Biochemical Laboratories, Inc.), and stirred for one hour. After cooling down, 19.3 g of the functional powdery product supporting glycosyl-hesperidin was collected by filtration and dried. The chromatic valence was 5.49.

Example 4

Functional Powdery Product 19.7 g of the functional powdery product supporting glycosyl-hesperidin ("αG-HESPERIDIN", commercialized by Hayashibara Biochemical Laboratories, Inc.) obtained according to the method in Example 2 except of using chitosan instead of crystalline cellulose. The product had chromatic valence of 8.48.

Example 5

Functional Powdery Product

Twenty grams of crystalline cellulose ("AVICEL PH-M06", commercialized by Asahi Kasei Corporation) was admixed with 45 ml of purified water, stirred at an inner temperature of 10-15° C., admixed once with 5 ml of purified water containing 0.5 g of glycosyl-rutin ("αG-RUTIN", commercialized by Hayashibara Biochemical Laboratories, Inc.) and 0.5 g of glycosyl-hesperidin ("αG-HESPERIDIN", commercialized by Hayashibara Biochemical Laboratories, Inc.), and stirred at the same temperature for 2 hours. After stirring the resulting solution at an ambient temperature, 19.0 g of the functional powdery product supporting glycosyl-rutin and glycosyl-hesperidin was collected by filtration and dried.

Example 6

Functional Powdery Product

Twenty grams of crystalline cellulose ("AVICEL PH-M06", commercialized by Asahi Kasei Corporation) was admixed with 45 ml of purified water, stirred at an inner temperature of 90° C., admixed with 7 ml of solution prepared by dissolving 1 g of glycosyl-naringin, prepared by the method disclosed in Example A-2 in patent literature No. 3, in 7 ml of purified water heated at 100° C. and cooling to 90° C., and stirred for about one hour. 19.2 g of the functional powdery product supporting glycosyl-naringin was collected by filtration and dried.

Example 7

Functional Powdery Product

Twenty grams of crystalline cellulose ("AVICEL PH-M06", commercialized by Asahi Kasei Corporation) was admixed with 45 ml of purified water, stirred at an inner temperature of 30° C., admixed with 3 ml of purifies water prepared by dissolving 1 g of L-ascorbic acid 2-glucoside (commercialized by Hayashibara Biochemical Laboratories, Inc.) and heating at 30° C., and stirred for about one hour. 19.0 g of the functional powdery product supporting L-ascorbic acid 2-glucoside was collected by filtration and dried.

Example 8

Additives Containing the Functional Powdery Products for External Dermatological Agent Two parts by weight of any one of the functional powdery product, prepared in Examples 1-7, was homogeneously admixed with one part by weight of α,α-trehalose monohydrate cosmetic grade (commercialized by Hayashibara Biochemical Laboratories, Inc.) and one part by weight of ascorbic acid 2-glucoside (commercialized by Hayashibara Biochemical Laboratories, Inc.) to obtain additives for external dermatological agent, which contains the functional powdery product supporting glycosyl-rutin, glycosyl-hesperidin, glycosyl-naringin and/or ascorbic acid 2-glucoside. Since the product contains α,α-trehalose, the functional powdery product is inhibited in solidification, hygroscopicity and deterioration. The product can be used alone as a raw material for external dermatological agent in a powdery, solid or solid powdery form. In case of other forms, it can be incorporated in an external dermatological agent by a suitable method depending on their forms.

Example 9

Additives Containing the Functional Powdery Products for External Dermatological Agent Any one of the functional powdery products, prepared in Examples 1-7, was homogeneously admixed with equal amount of saccharide derivatives of α,α-trehalose powder to obtain additives for external dermatological agent, which contains the functional powdery product supporting glycosyl-rutin, glycosyl-hesperidin, glycosyl-naringin and/or ascorbic acid 2-glucoside. Since the product contains saccharide derivatives of α,α-trehalose, the functional powdery product is inhibited in solidification, hygroscopicity and deterioration. The product can be used alone as a raw material for external dermatological agent in a powdery, solid or solid powdery form. In case of other forms, it can be incorporated in an external dermatological agent by a suitable method depending on their forms.

The above powdery saccharide derivatives of α,α-trehalose used in Example 9 for external dermatological agent was prepared by the following method. A corn starch was prepared into an about 20% of starch suspension, admixed with calcium carbonate to give a final concentration of 0.1%, and adjusted to pH 6.5. The resulting solution was admixed with 0.2%/g-starch on a dry solid basis of "TERMAMYL 60L", an α-amylase commercialized by NovoZyme A/S, Bagsverd, Denmark, and followed by the enzyme reaction at 95° C. for 15 minutes. After autoclaved at 120° C. for 10 minutes, the resulting reaction mixture was cooled to 50° C., adjusted to pH 5.8, admixed with 5 units/g-starch of maltotetraose-forming amylase disclosed in Japanese Patent Kokai No. 240,784/88, commercialized by Hayashibara Biochemical Laboratories Inc., Okayama, Japan, and 500 units/g-starch of isoamylase commercialized by Hayashibara Biochemical Laboratories Inc., and followed by the enzymatic reaction for 48 hours. The reaction mixture was further admixed with 30 units/g-starch of "α-AMYLASE 2A", α-amylase commercialized by Ueda Chemical Industries Co., Ltd. and followed by the enzyme reaction at 65° C. for four hours. After autoclaved at 120° C. for 10 minutes, the reaction mixture was cooled to 45° C., admixed with 2 units/g-starch of a non-reducing saccharide-forming enzyme originated from *Arthrobacter* sp. Q36 (FREM BP-4316), disclosed in Japanese Patent Kokai No. 143,876/95, and followed by an enzymatic reaction for 48 hours. The reaction mixture was kept at 95° C. for 10 minute, cooled and filtered to obtain a filtrate. According to conventional manner, the resulting filtrate was decolored with activated charcoal, desalted and purified with ion exchangers in H— and OH— forms, and concentrated into 70% syrup in a yield of about 90% to the material starch on a dry solid basis. The syrup contained about 53% of α,α-maltosyl α,α-trehalose, 10% of other saccharide derivatives of α,α-trehalose, about 37% sugar alcohols such as sorbitol, maltitol, maltotriitol and maltotetraitol. The syrup was spray-dried in a usual manner to obtain powdery saccharide derivatives of α,α-trehalose.

External Dermatological Agent Containing the Functional Powdery Product

Example 10

| Powder foundation | |
|---|---|
| Titanium oxide | 5 parts by weight |
| Anhydrous silic acid | 2 parts by weight |
| Corn starch | 4 parts by weight |
| α-Maltotriosyl α,α-trehalose (produced by Hayashibara Biochemical Laboratories, Inc.) | 1 part by weight |
| Silicon oil | 2 parts by weight |
| Diisostearylmalate | 1 part by weight |
| Neo-pentylglycol dioctanate | 1 part by weight |
| Squalane | 2 parts by weight |
| Functional powdery product supporting glycosyl-rutin, prepared in Example 1 | 1 part by weight |
| Functional powdery product supporting glycosyl-naringin, prepared in Example 6 | 3 parts by weight |
| Silicon powder | 10 parts by weight |
| Sericite | 68 parts by weight |

According to the above formula, a powder foundation was produced in a usual manner. Since the product contains the functional powdery product supporting glycosyl-rutin and glycosyl-naringin, glycosyl-rutin and glycosyl-naringin kept on or gradually released from the functional powdery product absorb UV to inhibit the productions of active oxygen and lipid peroxides in skins. Therefore, it can be used for the purpose of inhibiting the generation of wrinkles of face including expression wrinkles and continues the effect on inhibiting aging of skins, and keeps elasticity and no dullness of skins. The product is also advantageously in view of safety because of suppressing rough skin or inflammation due to anti-inflammatory activity of glycosyl-rutin and glycosyl-naringin.

Example 11

| Powder foundation | |
|---|---|
| Talc | 20 parts by weight |
| Mica | 33 parts by weight |
| Caolin | 7 parts by weight |
| Nylon powder | 10 parts by weight |
| Titanium dioxide | 10 parts by weight |
| Mica titanium | 3 parts by weight |
| Zinc stearate | 1 part by weight |
| Red oxide of iron | 1 part by weight |
| Yellow oxide of iron | 1 part by weight |
| water-insoluble chitosan powder supporting Shikon black dye | 3 parts by weight |
| Additive for dermatological external agent containing the functional powdery product supporting glycosyl-hesperidin, prepared in Example 9 | 4 parts by weight |
| Squalane | 6 parts by weight |
| Lanolin acetate | 1 part by weight |
| Octyldodecyl myristate | 2 parts by weight |
| Perfumeries | suitable amount |
| Antiseptics | suitable amount |

According to the above formula, a powder foundation was produced in a usual manner. Since the product contains the functional powdery product supporting glycosyl-hesperidin, the glycosyl-hesperidin kept on or gradually released from the functional powdery product absorb UV to inhibit the productions of active oxygen and lipid peroxides in skins. Therefore, it can be used for the purpose of inhibiting the generation of wrinkles of face including expression wrinkles and continues the effect on inhibiting aging of skins, and keeps elasticity and no dullness of skins. The product is a solid powder cosmetic having satisfactory gloss and no sticky feeling, easily softening off its color, having satisfactory adhesion feeling and no light of a membranous oil, further hardly dissolved by sweet or sebum and having satisfactory long-lasting and skin feeling. The product is also advantageous in view of safety because of suppressing rough skin or inflammation due to anti-inflammatory activity of glycosyl-rutin and glycosyl-naringin.

Example 12

| Foundation | |
|---|---|
| Purified water | 66 parts by weight |
| Glycerin | 4.7 parts by weight |
| Additive containing the functional powdery product supporting glycosyl-hesperidin for external dermatological agent, prepared in Example 9 | 7 parts by weight |
| Propyleneglycol | 7 parts by weight |
| Titanium dioxide | 2 parts by weight |
| Squalane | 3 parts by weight |
| Cetyl-2-ethylhexanoate | 3 parts by weight |
| Vaseline | 1 part by weight |
| Red oxide of iron | 0.01 part by weight |
| Yellow oxide of iron | 0.01 par by weight |
| Water-insoluble chitosan powder supporting shikon dye produced according to the method described in Example 1 in Japanese Patent No. 2815026 specification (produced by Hayashibara Biochemical Laboratories, Inc.) | 0.07 part by weight |

-continued

| Foundation | |
|---|---|
| Sodium hexametaphosphate | 0.01 part by weight |
| Sodium hydroxide | 0.2 part by weight |
| Cetostearyl alcohol | 3 parts by weight |
| Stearic acid | 2 parts by weight |
| Glycerylmonostearate | 2 parts by weight |
| Perfumeries | suitable amount |
| Antiseptics | suitable amount |

According to the above formula, a foundation was produced in a usual manner. Since the product contains the functional powdery product supporting glycosyl-hesperidin, the glycosyl-hesperidin kept on or gradually released from the functional powdery product absorb UV to inhibit the productions of active oxygen and lipid peroxides in skins. Therefore, it can be used for the purpose of inhibiting the generation of wrinkles of face including expression wrinkles and continues the effect on inhibiting aging of skins, and keeps elasticity and no dullness of skins. Since the product also contains saccharide derivatives of α,α-trehalose, it is a satisfactory cosmetic foundation without sticky feeling. The product is advantageous in view of safety because of suppressing rough skin or inflammation due to anti-inflammatory activity of glycosyl-hesperidin. Further, it has so satisfactory thermostability that its smell and shape are not changed even if kept at a high temperature for a long period of time.

Example 13

| Eyeliner | |
|---|---|
| Vinyl acetate plastic emulsion | 45 parts by weight |
| Glycerin | 3 parts by weight |
| Saccharide derivatives of α,α-trehalose in a syrupy form used in Example 9 | 2 parts by weight |
| Carboxymethylcellulose (10% aqueous solution) | 2 parts by weight |
| Polyoxyethylene sorbitan monooleate ester | 1 part by weight |
| Purified water | 19 parts by weight |
| Chitosan powder supporting shikon black dye ("SHIKON BLACK CHITOFINE POWDER", produced by Hayashibara Biochemical Laboratories, Inc.) | 15 parts by weight |
| Powder consisting of silk powder supporting gardenia dye ("UJO GARDENIA POWDER", commercialized by Hayashibara Biochemical Laboratories, Inc.) | 1 part by weight |
| Additive for external dermatological agent, containing the functional powdery product supporting glycosyl-hesperidin, prepared in Example 8 | 2 parts by weight |
| Perfumeries | suitable amount |
| Antiseptics | suitable amount |

According to the above formula, eyeliner was produced in a usual manner. Since the product contains the functional powdery product supporting glycosyl-hesperidin, the glycosyl-hesperidin kept on and gradually released from the functional powdery product absorbs UV to inhibit the productions of active oxygen and lipid peroxides in skin and increase blood-flow in skin of eye's edge and lid thereof. Therefore, it can be used for the purpose of inhibiting the generation of wrinkles of face including expression wrinkles and continues the effect on inhibiting aging of skins, and keeps elasticity and no dullness of skins. Since the product also contains saccharide derivatives of α,α-trehalose, it is a satisfactory cosmetic foundation without sticky feeling. The product is advantageously in view of safety because of suppressing rough skin or inflammation due to anti-inflammatory activity of glycosyl-hesperidin. Further, it has so satisfactory thermostability that its smell and shape are hardly changed even if kept at a high temperature for a long period of time.

Example 14

| Sunscreen | |
|---|---|
| Purified water | 35 parts by weight |
| 1,3-Butyleneglycol | 5 parts by weight |
| Squalane paramethoxycinnamic octyl | 6 parts by weight |
| Oxybenzene | 3 parts by weight |
| Hydrophobic treating titanium dioxide | 3 parts by weight |
| Glycerin diisostearate | 3 parts by weight |
| Ascorbic acid 2-glucoside (Commercialized by Hayashibara Biochemical Laboratories, Inc.) | 2 parts by weight |
| Powder consisting of water-insoluble chitin supporting shikon black dye ("SHIKON CA BLACK CHITOFINE POWDER", commercialized by Hayashibara Biochemical Laboratories, Inc.) | 0.5 part by weight |
| Additive containing the functional powdery product supporting glycosyl-rutin, prepared in Example 9 | 3 parts by weight |
| Organic-modified montmorillonite | 1.5 parts by weight |

According to the above formula, a sunscreen was produced in a usual manner. Since the product contains the functional powdery product supporting glycosyl-rutin kept on or gradually released from the functional powdery product absorbs UV to inhibit the productions of active oxygen and lipid peroxides in skins and prevents sunburn. Therefore, it can be used for the purpose of inhibiting the generation of wrinkles of face including expression wrinkles and continues the effect on inhibiting aging of skins, and keeps elasticity and no dullness of skins. Since the functional powdery product absorbs UV, it is a satisfactory inhibiting effect on sunburn. The product is advantageous in view of safety because of suppressing rough skin or inflammation due to anti-inflammatory activity of glycosyl-rutin.

Example 15

| Lipstick | |
|---|---|
| Functional powdery product supporting glycosyl-hesperidin, prepared by the method in Example 3 | 1 part by weight |
| Titanium dioxide | 3.5 parts by weight |
| Blue No. 1 | 1 part by weight |
| Black iron oxide | 0.1 part by weight |
| Red iron oxide | 1.5 parts by weight |
| Castor oil | 25 parts by weight |
| Candelilla wax | 8 parts by weight |
| Solid paraffin | 8 parts by weight |
| Yellow beewax | 5 parts by weight |
| Carnauba wax | 5 parts by weight |
| Lanoline | 11 parts by weight |
| Cetyl-2-ethylhexanoate | 20 parts by weight |
| Isopropylmyristate | 10 parts by weight |
| Antioxidant | suitable amount |
| Perfumeries | suitable amount |

According to the above formula, a lipstick was prepared by a conventional method. Since the product comprises a functional powdery product supporting glcosyl-hesperidin, glycosyl-hesperidin on the functional powdery product or that gradually releasing from the functional powdery product absorb ultraviolet radiation, increase vascular flow of the lips and skin around lips, and inhibit the generation of active oxygen and lipid peroxide. Therefore, since the product inhibits the formation of wrinkles of the lips and skin around the lips and keeps aging-retardant effects for a long period of time, it can be used for keeping lips condition to exhibit good texture and no wrinkles and dullness. Further, since glycosyl-hesperidin exhibits anti-inflammatory effect, the product has a satisfactory safety without causing skin roughness and inflammation even when applied on the lips. Furthermore, the product has a satisfactory thermal stability without causing deterioration of scent and deformation even when left under a high-temperature condition for a long period of time.

Example 16

| Lipstick | |
| --- | --- |
| Functional powdery product supporting glycosyl-rutin, prepared by the method in Example 2 | 1 part by weight |
| Titanium oxide | 3.5 parts by weight |
| Red No. 201 | 0.5 part by weight |
| Red No. 202 | 2 parts by weight |
| Red No. 223 | 0.05 part by weight |
| Candelilla wax | 8 parts by weight |
| Castor oil | 30 parts by weight |
| Cetyl-2-ethylhexanoate | 20 parts by weight |
| Cerecin | 4 parts by weight |
| Carnauba wax | 2 parts by weight |
| Lanoline | 11 parts by weight |
| Isostearic acid diglyceride | 40 parts by weight |
| Polyoxyethylene (25) plyoxypropylene (20) 2-tetradecylether | 1 part by weight |
| Saccharide-derivative of α,α-trehalose in a syrupy form, used in Example 9 | 2 parts by weight |
| Glycosyl-hesperidin | 1 part by weight |
| Purified water | 4 parts by weight |

According to the above formulation, a lipstick was prepared by a conventional method. Since the product comprises a functional powdery product supporting glcosyl-rutin, glycosyl-hesperidin on the functional powdery product or that gradually releasing from the functional powdery product and/or glycosyl-hesperidin absorb ultraviolet radiation, increase vascular flow of the lips and skin around the lips, and inhibit the generation of active oxygen and lipid peroxide. Therefore, since the product inhibits the formation of wrinkles of the lips and skin around the lips and keeps aging-retardant effects for a long period of time, it can be used for keeping the lips in condition to exhibit good texture and no wrinkles and dullness. Also, since the product comprises saccharide-derivatives of α,α-trehalose, it gives a good gloss, nonsticky, and a satisfactory makeup-retaining effect and sense of use. In addition, saccharide-derivatives of α,α-trehalose, glycosyl-rutin and glycosyl-hesperidin exhibit antioxidative effect and anti-inflammatory effect, the product has a satisfactory safety without causing skin roughness and inflammation even when applied on to the lips. Furthermore, a solid powdery cosmetic of the present invention has a satisfactory thermal stability without causing deterioration of scent and deformation even when left under a high-temperature condition for a long period of time.

Example 17

| Eye shadow | |
| --- | --- |
| Talc | 45 parts by weight |
| Mica | 15 parts by weight |
| Sericite | 5 parts by weight |
| Water-insoluble chitosan powder supporting shikonin prepared by the method described in Japanese Patent No. 2,815,026 (produced by Hayashibara Biochemical Laboratories Inc., Okayama, Japan) | 12 parts by weight |
| Black ferric oxide | 3 parts by weight |
| Pearl pigment | 10 parts by weight |
| Functional powdery product supporting for glycosyl-naringin, prepared by the method in Example 6 | 2 parts by weight |
| Liquid paraffin | 6 parts by weight |
| Methylpolysiloxane | 2 parts by weight |
| Sesquioreic acid sorbitan | 2 parts by weight |

According to the above formula, an eye shadow was prepared by a conventional method. Since the product comprises functional powdery product supporting glcosyl-naringin, glycosyl-naringin on the functional powdery product or that gradually releasing from the functional powdery product absorb ultraviolet radiation, inhibit the generation of active oxygen and lipid peroxide of eyelid, tail of eye and skin around them, and strengthen cappillary vessel. Therefore, since the product inhibits the formation of wrinkles and sagging of eyelids and keeps aging-retardant effects for eyelid for a long period of time, it can be used for keeping eyelids condition to exhibit good texture and no wrinkles and dullness. Also, the product is a solid powdery cosmetic with a good gloss, nonsticky, and a satisfactory makeup-retaining effect and sense of use without causing the generation of roughness and inflammation of skin. Furthermore, the product has a satisfactory thermal stability without causing deterioration of scent and deformation even when left under a high-temperature condition for a long period of time.

Example 18

| Eye shadow | |
| --- | --- |
| Additive for external dermatological agent, comprising functional powdery product supporting glycosyl-rutin and glycosyl-hesperidin, prepared by the method in Example 8 | 5 parts by weight |
| Talc | 46 parts by weight |
| Mica | 16 parts by weight |
| Sericite | 5 parts by weight |
| Pearl pigment | 10 parts by weight |
| Liquid paraffin | 6 parts by weight |
| Methylpolysiloxane | 5 parts by weight |
| Sesquioreic acid sorbitan | 3 parts by weight |
| Black ferric oxide | 3 parts by weight |
| Silk powder supporting SHIKON dye ("UJO-SHIKON POWDER", commercialized by Hayashibara Biochemical Laboratories Inc., Okayama, Japan) | 1 part by weight |

According to the above formula, an eye shadow was prepared by a conventional method. Since the product comprises functional powdery product supporting glcosyl-rutin and glycosyl-hesperidin, glycosyl-rutin and glycosyl-hesperidin on the functional powdery product or those gradually releasing from the functional powdery product absorb ultraviolet radiation, inhibit the generation of active oxygen and lipid peroxide of skin, and strengthen cappillary vessel. Therefore, since the product inhibits the formation of wrinkles and sagging of eyelids and keeps aging-retardant effects for eyelid for a long period of time, it can be used for keeping eyelids condition to exhibit good texture and no wrinkles and dullness. Also, since the product comprises α,α-trehalose as an ingredient of additives for external dermatological agent, the product is a non-sticky solid powdery cosmetic which exhibits a satisfactory gloss, adhesion strength, makeup-retaining effect and sense of use. Further, the product shows no oily light, hardly runs by sweat and sebum and can be graded easily. In addition, since α,α-trehalose, glycosyl-rutin and glycosyl-hesperidin inhibit skin roughness and inflammation, the product has a satisfactory safety. Furthermore, the product has a satisfactory thermal stability without causing deterioration of scent and deformation even when left under a high-temperature condition for a long period of time.

Example 19

| Oily suntan cosmetic | |
| --- | --- |
| Liquid paraffin | 68 parts by weight |
| Cetyloctanoate | 28 parts by weight |
| Additive for external dermatological agent, comprising functional powdery product supporting glycosyl-rutin, prepared by the method in Example 9 | 2 parts by weight |

According to the above formula, an oily suntan cosmetic was prepared by a conventional method. Since the product comprises functional powdery product supporting glycosyl-rutin, glycosyl-rutin on the functional powdery product or that gradually releasing from the functional powdery product absorbs ultraviolet radiation and inhibits the generation of active oxygen and lipid peroxide, which are caused by sunburn, the product inhibits the formation of wrinkles of face and keeps its skin-aging-retardant effect for a long period of time. Therefore, the product can be used for keeping skin condition to exhibit good texture and no dullness. Also, since the powdery product supporting glycosyl-rutin absorbs ultraviolet radiation, the product can be used for preventing sunburn. Furthermore, since roughness and inflammation of skin are inhibited by anti-inflammatory effects of saccharide-derivatives of α,α-trehalose and glycosyl-rutin, which are comprised in additives for external dermatological agent, the product has a satisfactory safety.

Example 20

| Soap | |
| --- | --- |
| Neat soap obtained by conventional saponification-salting out method from a mixture of beef tallow and palm oil (4 parts and 1 part by weight) | 96.5 parts by weight |
| Saccharide-derivatives of α,α-trehalose in a syrupy form, used in Example 9 | 1.5 parts by weight |
| Ascorbic acid 2-glucoside (commercialized by Hayashibara Biochemical Laboratories Inc., Okayama, Japan) | 0.5 part by weight |
| Sucrose | 0.5 parts by weight |
| Functional powdery product supporting for glycosyl-hesperidin, prepared by the method in Example 3 | 0.5 part by weight |
| Functional powdery product supporting for L-ascorbic acid 2-glucoside, prepared in Example 7 | 0.5 parts by weight |
| Maltitol | 1 part by weight |
| Cellulose powder supporting Safflower-red dyed cellulose powder ("BENIBANA-AKA CELLULOSE POWDER", commercialized by Hayashibara Biochemical Laboratories Inc., Okayama, Japan) | |
| KANKO-SO No. 201 | 0.0001 part by weight |
| Perfumeries | suitable amount |

According to the above formula, soap was prepared by a conventional method. Since the product comprises a functional powdery product supporting glycosyl-hesperidin, it can be used for inhibiting the generation of active oxygen and lipid peroxide in skin and strengthening capillary vessel by a synergy effect of glycosyl-hesperidin supported on the functional powdery product or that released from the functional powdery product and saccharide-derivatives of α,α-trehalose incorporated. Therefore, the product is a soap kind to the skin, which can be used for inhibiting skin roughness and inflammation of skin. Further, since the product comprises saccharide-derivatives of α,α-trehalose, it has a satisfactory transparency even though it comprises saccharides.

Example 21

| Cosmetic cream | |
| --- | --- |
| (Formula 1) | |
| Polyoxyethyleneglycol monostearate | 2 parts by weight |
| Self-emulsifying glycerin monostearate | 5 parts by weight |
| Potassium DL-lactate | 5 parts by weight |
| Behenylalcohol | 1 part by weight |
| Eicosatetraenoic acid | 2 parts by weight |
| Liquid paraffin | 1 part by weight |
| Functional powdery product supporting for glycosyl-rutin, prepared by the method in Example 1 | 2 parts by weight |
| Glycerin trioctanoate | 10 parts by weight |
| Preservative | suitable amount |
| (Formula 2) | |
| Glycerin | 2 parts by weight |
| 1,3-Butyleneglycol | 5 parts by weight |
| Purified water | 66 parts by weight |
| Perfumeries | suitable amount |

According to Formula 1, ingredients described above were mixed and dissolved by heating by a conventional method. After mixing ingredients in Formula 2 except for fragrance to the above mixture, the resulting mixture was emulsified using a homogenizer, admixed with fragrance and further mixed with stirring to make into a cosmetic cream. Since the product comprises a functional powdery product supporting glycosyl-rutin, glycosyl-rutin supported on the functional powdery product or that released from the functional powdery product absorbs ultraviolet radiation and increases blood flow of skin. Also, since glycosyl-rutin inhibits the generation of active oxygen and lipid peroxide and the formation of blood vessels, one of cause of wrinkle formation, the product can be used for preventing the aging of skin. Further, since the product inhibits the oxidation and decomposition of lipids from sweat, grime, scurf, and sebum, it can be advantageously used for lowering body odor, preventing stimulation of the skin, and the itch, and curing or preventing pigmentation such as pigmented spot, freckle, and sunburn. The product is a cosmetic cream with a satisfactory sense of use and nonsticky even when applied on the skin.

Example 22

| Cosmetic cream | |
| --- | --- |
| (Formula 1) | |
| Polyoxyethyleneglycol monostearate | 2 parts by weight |
| Self-emulsifying glycerin monostearate | 5 parts by weight |
| Potassium DL-lactate | 5 parts by weight |
| Behenylalcohol | 1 part by weight |
| Eicosatetraenoic acid | 2 parts by weight |
| Liquid paraffin | 1 part by weight |
| Glycerin trioctanoate | 10 parts by weight |
| Ascorbic acid 2-glucoside | 2 parts by weight |
| Preservative | suitable amount |
| (Formula 2) | |
| Saccharide-derivative of α,α-trehalose in a syrupy form, used in Example 9 | 1.6 parts by weight |
| Sodium hyaluronate | 0.1 part by weight |
| Dipotassium glycyrrhizinate | 0.1 parts by weight |
| Aloe vera extract | 0.1 part by weight |
| Balm mint extract | 0.05 part by weight |
| Chamomilla recutita extract | 0.05 part by weight |
| Functional powdery product supporting for glycosyl-rutin, prepared by the method in Example 2 | 1 part by weight |
| Polygonum tinctorium aqueous extract (produced by Hayashibara Biochemical Laboratories Inc., Okayama, Japan) | 1 part by weight |
| 1,3-Butyleneglycol | 5 parts by weight |
| Purified water | 66 parts by weight |

According to Formula 1, ingredients described above were mixed and dissolved by heating by a conventional method. After mixing ingredients in Formula 2 to the above mixture, the resulting mixture was emulsified using a homogenizer, admixed with suitable amount of fragrance and further mixed with stirring to make into a cosmetic cream. Since the product comprises a functional powdery product supporting glycosyl-rutin, glycosyl-rutin supported on the functional powdery product or that released from the functional powdery product absorbs ultraviolet radiation and increases blood flow to the skin. Also, since glycosyl-rutin inhibits the generation of active oxygen and lipid peroxide and the formation of blood vessel, one of cause of wrinkle formation, the product can be used for preventing the aging of skin. Further, since the product inhibits the oxidation and decomposition of lipids from sweat, grime, scurf, and sebum, it can be advantageously used for lowering body odor, preventing stimulation of the skin and the itch, and curing or preventing pigmentation such as pigmented spto, freckle, and sunburn. The product is a cosmetic cream with a satisfactory sense of use and nonsticky even when applied to the skin.

Example 23

| Cosmetic emulsion | |
| --- | --- |
| Stearic acid | 2.5 parts by weight |
| Cetanol | 1.5 parts by weight |
| Vaseline | 5 parts by weight |
| Liquid paraffin | 10 parts by weight |
| Polyoxyethylene oreate | 2 parts by weight |
| Tocopherol acetate | 0.5 part by weight |
| Dipotassium glycyrrhizinate | 0.2 part by weight |
| Polyethyleneglycol (1500) | 3 parts by weight |
| Ascorbic acid 2-glucoside | 3 parts by weight |
| Polygonum tinctorium aqueous extract | 3 parts by weight |
| Additive for external dermatological agent, comprising functional powdery product supporting glycosyl-rutin, prepared by the method in Example 9 | 5 parts by weight |
| | 4 parts by weight |
| Triethanolamine | 1 part by weight |
| Purified water | 66 parts by weight |
| Propylparaben | 0.1 part by weight |

According to Formulae, ingredients were mixed, adjusted to pH 6.7 by potassium hydroxide, and admixed with suitable amount of fragrance to make into a cosmetic emulsion. According to Formula 1, ingredients described above were mixed and dissolved by heating by a conventional method. After mixing ingredients in Formula 2 except for fragrance to the above mixture, the resulting mixture was emulsified using a homogenizer, admixed with fragrance and further mixed with stirring to make into a cosmetic emulsion. Since the product comprises a functional powdery product supporting glycosyl-rutin, glycosyl-rutin supported on the functional powdery product or that released from the functional powdery product absorbs ultraviolet radiation and increases blood flow of skin. Also, since glycosyl-rutin inhibits the generation of active oxygen and lipid peroxide and the formation of blood vessel, one of cause of wrinkle formation, the product can be used for preventing the aging of skin. Further, since the product inhibits the oxidation and decomposition of lipids from sweat, grime, scurf, and sebum, it can be advantageously used for lowering body odor, preventing stimulation of the skin and the itch, and curing or preventing pigmentation such as pigmented spot, freckle, and sunburn. The product is a cosmetic emulsion with a satisfactory sense of use and nonsticky even when applied on the skin.

Example 24

| Conditioner (rinse) | |
| --- | --- |
| (Formula 1) | |
| Liquid paraffin | 2.5 parts by weight |
| Myristic acid | 0.5 part by weight |
| Cetanol | 1.5 parts by weight |
| Glycerin monostearate | 3 parts by weight |
| Polyoxyethylene octyldodecyletherdiester lauroyl glutamate | 1 part by weight |
| Functional powdery product supporting glycosyl-rutin, prepared in Example 1 | 4 parts by weight |
| Polyoxyethyleneglyceril pyroglutamate isostearate | 0.5 part by weight |
| Photosensitizing dye No. 301 | 0.1 part by weight |

-continued

Conditioner (rinse)

(Formula 2)

| | |
|---|---|
| Glycerin | 3 parts by weight |
| Lauroyl-L-lysine | 2.5 parts by weight |
| Fatty acid-L-arginieethylpyroridon carbonic acid salt | 0.5 part by weight |
| Stearyltrimethylammonium chloride | 0.5 part by weight |
| Glycosyl-naringin | 0.1 part by weight |
| Sodium pyroridoncarnonate | 1 part by weight |
| Purified water | 75 parts by weight |

According to the above formulae, a mixture prepared by mixing ingredients of Formula 1 by heating and another mixture prepared by mixing ingredients of Formula 2 by heating were mixed and emulsified by a conventional method to make into a conditioner. Since the product comprises a functional powdery product supporting glycosyl-rutin, glycosyl-rutin supported on the functional powdery product or that released from the functional powdery product absorbs ultraviolet radiation and increases blood flow of skin. Also, since glycosyl-rutin inhibits the generation of active oxygen and lipid peroxide and the formation of blood vessel, one of cause of wrinkle formation, the product can be used for preventing the aging of skin.

Example 25

Shampoo

| | |
|---|---|
| 2-Alkyl-N-carboxymethyl-N-hydroxymethyl-imidazolium betain (30% aqueous solution) | 35 parts by weight |
| Palm oil-fatty acid triethanolamine glutamate solution (30% aqueous solution) | 35 parts by weight |
| Saccharide-derivatives of α,α-trehalose in a syrupy form, used in Example 9 | 10 parts by weight |
| Potassium cocoyl glycinate (30% aqueous solution) | 10 parts by weight |
| Palm oil-fatty acid diethanolamide | 2.3 parts by weight |
| Functional powdery product supporting for glycosyl-hesperidin, prepared in Example 3 | 3 parts by weight |
| Photosensitizing dye No. 201 | 0.1 part by weight |
| Photosensitizing dye No. 301 | 0.1 part by weight |
| Purified water | 10 parts by weight |

According to the above formula, these ingredients were mixed and dissolved by heating to 70° C. during stirring, and then admixed with a suitable amount of fragrance by a conventional method to make into a shampoo. Since the product comprises a functional powdery product supporting glycosyl-hesperidin, glycosyl-rutin supported on the functional powdery product or that released from the functional powdery product increases blood flow to the skin. Also, since glycosyl-rutin inhibits the generation of active oxygen and lipid peroxide, the product can be used for preventing the aging of skin. Since the unpleasant smell derived from ingredients such as emulsifiers and the unpleasant taste, which is felt when a person put it in his mouth, are reduced, the product is a shampoo with a satisfactory foaming activity and sense of use. In addition, since the product inhibits the formation of amines and aldehydes and/or the oxidation and decomposition of lipids, it can be advantageously used for preventing the formation of nasty odors originated from scalp and sebum, preventing itch, inhibiting the formation of scurf, and curing or preventing the aging of scalp. Further, since the product comprises saccharide-derivatives of α,α-trehalose, it exhibits a satisfactory moisture-retaining activity and a low skin-irritating property compared with a shampoo prepared by using glycerin. Therefore, the product can be used without concerning hypersensitivity.

Example 26

Hair treatment (Formula 1)

| | |
|---|---|
| Stearylalcohol | 5 parts by weight |
| Glycerin monostearate | 5 parts by weight |
| Liquid paraffin | 3.5 parts by weight |
| Polyoxyethylene octyldodecyletherdiester lauroyl glutamate | 2 part by weight |
| Polyoxyethyleneglyceril pyroglutamate isostearate | 1 part by weight |

(Formula 2)

| | |
|---|---|
| Saccharide-derivatives of α,α-trehalose in a syrupy form, used in Example 9 | 5 parts by weight |
| 1,3-Butyleneglycol | 3 parts by weight |
| Stearyltrimethylammonium chloride | 1 part by weight |
| Sodium pyroridoncarbonate | 1 part by weight |
| Functional powdery product supporting glycosyl-rutin, prepared in Example 1 | 0.4 part by weight |
| Functional powdery product supporting L-ascorbic acid 2-glucoside, prepared in Example 7 | 0.4 part by weight |
| Deionized water | 65 parts by weight |

According to the above formulae, ingredients in Formula 1 and Formula 2 were respectively mixed during heating. Successively, both mixtures were mixed and emulsified by a conventional method to make into a hair treatment. Since the product comprises two functional powdery products respectively supporting glycosyl-rutin and ascorbic acid 2-glucoside, glycosyl-rutin and ascorbic acid 2-glucoside supported on the functional powdery products or those released from the functional powdery products increase blood flow of skin. Also, since glycosyl-rutin and ascorbic acid 2-glucoside inhibit the generation of active oxygen and lipid peroxide, the product can be used for preventing the aging of skin. Further, since the product comprises saccharide-derivatives of α,α-trehalose, the unpleasant smell derived from ingredients such as emulsifiers and the unpleasant taste, which is felt when a person put it in his mouth, are reduced. Therefore, the product is a hair treatment exhibiting a satisfactory moisture-retaining activity, a low skin-irritating property, and a satisfactory sense of use.

Example 27

Ointment for curing wound (Formula 1)

| | |
|---|---|
| Macrogol (400) | 50 parts by weight |
| Carboxyvinyl polymer | 3 parts by weight |
| Pullulan | 1 part by weight |
| Isopropanol | 400 parts by weight |
| Chlorhexidine gluconate solution | 1 part by weight |
| Functional powdery product supporting for glycosyl-rutin, prepared by the method in Example 2 | 2 parts by weight |

(Formula 2)

| | |
|---|---|
| Saccharide-derivatives of α,α-trehalose | 80 parts by weight |

| Ointment for curing wound | |
|---|---|
| in a syrupy form, used in Example 9 | |
| Sodium hydroxide | 3 parts by weight |
| Purified water | 67 parts by weight |

According to the above formulae, ingredients in Formula 1 were mixed during stirring in vacuo by a conventional method. Successively, ingredients in Formula 2 were mixed to the above mixture to make into an ointment for curing wound which exhibits adequate extendability and adhesiveness. Since the product comprises functional powdery product supporting glycosyl-rutin, glycosyl-rutin supported on the functional powdery product or that released from the functional powdery product inhibits the generation of active oxygen and lipid peroxide, and prevents inflammation of the skin. Since the product comprises saccharide-derivatives of α,α-trehalose, the unpleasant smell derived from ingredients and the unpleasant taste, which is felt when a person put it in his mouth, are reduced. The product exhibits a satisfactory sense of use and can be used for curing wounds such as incised wound, scratch, burn injury, athlete's foot and chilblain by applying it to wound directly or with using gauzes.

INDUSTRIAL APPLICABILITY

The functional powdery product of the present invention, which is prepared by allowing a carrier such as saccharides to support one or more members selected from vitamin glycosides, can be incorporated easily in a powdery form to external dermatological agent in the forms of powder, solid or solid powder and enables to extend the uses of vitamin glycosides. In the case of incorporating the functional powdery product of the present invention into an external dermatological agent, vitamin glycosides supported on a carrier such as saccharides or those gradually released from the carrier contact to the skin. Since the vitamin glycosides exhibit activities of vitamins such as ultraviolet radiation-absorbing activity, antioxidative activity and antiinflammation activity and keep those activities for a long period of time, the external dermatological agent can be used for improving skin metabolism and inhibiting the formation of skin roughness and the aging of the skin, which are caused by inflammation of the skin and allergies. Also, since the vitamin glycosides inhibit inflammation of the skin, allergic reaction and the aging of the skin, the external dermatological agent can be used for inhibiting the formation of wrinkles, saggings, pigmented spots and skin dullness and keeping natural skin with a satisfactory texture. The present invention, having these outstanding functions and effects, is a significantly important invention that greatly contributes to this art.

The invention claimed is:

1. A functional powdery product, which is prepared by allowing a carrier to adsorb a vitamin glycoside by dissolving said vitamin glycoside in water containing said carrier in a suspended form, whereby said vitamin glycoside is homogeneously supported on the surface of said carrier,
wherein said carrier is a member selected from the group consisting of crystalline cellulose, cellulose powder, chitosan, silk powder, and mixtures thereof; and
said vitamin glycoside is a member selected from the group consisting of glycosyl rutin, glycosyl hesperidin, glycosyl naringin, L-ascorbic acid 2-glucoside, and mixtures thereof;
wherein the amount of said vitamin glycoside supported on the surface of the carrier is 0.01 to 30% w/w based on the amount of said functional powdery product, and
wherein the average particle size of said functional powdery product is 0.01 to 30 μm.

2. The functional powdery product of claim 1, wherein said vitamin glycoside is L-ascorbic acid 2-glucoside.

3. The functional powdery product of claim 1, wherein said carrier is silk powder.

4. An external dermatological agent, comprising the functional powdery product of claim 1.

5. The external dermatological agent of claim 4, which further contains one or more pharmaceutically acceptable substances as external dermatological agents along with the functional powdery product.

6. The external dermatological agent of claim 5, wherein said pharmaceutically acceptable substances are one or more members selected from the group consisting of powders other than the functional powdery product; substances which have circulation-promoting action, anti-inflammatory action, antibacterial action, moisture-retaining action, skin-whitening action, emulsifying action, ultraviolet-ray-absorbing action, ultraviolet-ray-scattering action, astriction, anti-wrinkle action, cell-activating action, or percutaneous-absorption-promoting action; and/or oils and fats.

7. The external dermatological agent of claim 6, wherein said powders other than the functional powdery product are one or more members selected from the group consisting of talc, kaolin, sericite, muscovite, synthetic mica, lepidolite, biotite, lithia mica, vermiculite, magnesium carbonate, calcium carbonate, diatomaceous earth, magnesium silicate, calcium silicate, aluminum silicate, barium silicate, strontium silicate, metal tungstate, α-iron oxide, hydrated iron oxide, silica, hydroxyapatite, α-maltotriosyl α,α-trehalose, dextrin, nylon powder, polyethylene powder, benzoguanamine powder, ethylene tetrafluoride powder, distilbene-pinhole-polymer powder, polyamide high molecular powder, agar powder, agarose powder, alginic acid powder, starch, modified starch, cellulose powder, chitin powder, chitosan powder, silk powder, casein powder, gelatin powder, titanium oxide, zinc oxide, iron oxide (red iron oxide), iron titanate, yellow oxide of iron, cobalt titanate, mango violet, cobalt violet, chromium oxide, chromium hydroxide, cobalt titanate, ultramarine, Prussian blue, titanium oxide coated bismuth oxychloride, bismuth oxychloride, titanium oxide coated mica, fish scale flake, colored titanium oxide coated mica, aluminum, copper, and powders of colorants supported on carriers.

8. The external dermatological agent of claim 7, wherein said carrier for colorants is one or more members selected from the group consisting of saccharides, proteins, and synthetic polymers.

9. The external dermatological agent of claim 7, wherein said colorants are one or more members selected from the group consisting of shikonin derivatives, gardenia yellow, safflower color, red beet color, and cochineal.

10. The external dermatological agent of claim 5, wherein said pharmaceutically acceptable substances are one or more members selected from the group consisting of monosaccharides, disaccharides, oligosaccharides, and sugar alcohols.

11. The external dermatological agent of claim 10, wherein said monosaccharides, disaccharides, oligosaccharides, and sugar alcohols are α,α-trehalose, α,β-trehalose, sorbitol, maltitol, maltotriitol, maltotetraitol, saccharide derivatives of α,α-trehalose, and cyclic tetrasaccharides.

12. The external dermatological agent of claim 4, which is in the form of a cosmetic, quasi-drug, or pharmaceutical.

13. The external dermatological agent of claim 4, which is any one of sunscreen oils, sunscreen lotions, sunscreen creams, creams, emulsions, cosmetic liquids, lotions, cosmetic oils, hair cosmetics, hair dyes, perfumes, kneaded perfumes, powdered perfumes, powders, packs, foundations, face powders, lipsticks, lipcreams, blushes/cheek colors, eye shadows, eye liners, mascaras, eye brows, nail creams, nail enamels, shampoos, rinses, hair treatments, hair colors, soaps, bath preparations, toothpastes, and mouthwashes.

14. The external dermatological agent of claim 4, which is in the form of a powder, semi-solid, solid, or solid powder.

* * * * *